United States Patent
Smith et al.

(10) Patent No.: US 7,420,724 B2
(45) Date of Patent: Sep. 2, 2008

(54) SCANNER APPARATUS HAVING ELECTROMAGNETIC RADIATION DEVICES COUPLED TO MEMS ACTUATORS

(75) Inventors: Stephen W. Smith, Durham, NC (US); Kenneth L. Gentry, Durham, NC (US); Jason Zara, Vienna, VA (US); Stephen M. Bobbio, Wake Forest, NC (US)

(73) Assignee: Duke University, Durham, NC (US)

( * ) Notice: Subject to any disclaimer, the term of this patent is extended or adjusted under 35 U.S.C. 154(b) by 298 days.

(21) Appl. No.: 10/380,791

(22) PCT Filed: Sep. 14, 2001

(86) PCT No.: PCT/US01/28765

§ 371 (c)(1),
(2), (4) Date: Oct. 22, 2003

(87) PCT Pub. No.: WO02/23251

PCT Pub. Date: Mar. 21, 2002

(65) Prior Publication Data

US 2004/0218244 A1    Nov. 4, 2004

Related U.S. Application Data

(60) Provisional application No. 60/233,262, filed on Sep. 18, 2000.

(51) Int. Cl.
*G02B 26/08* (2006.01)
(52) U.S. Cl. .................. 359/224; 359/198; 359/199
(58) Field of Classification Search ......... 359/198–199, 359/224
See application file for complete search history.

(56) References Cited

U.S. PATENT DOCUMENTS 5,182,910 A    2/1993    Benecke ................. 60/529

(Continued)

FOREIGN PATENT DOCUMENTS

EP    0742459 A1    11/1996

(Continued)

OTHER PUBLICATIONS

Butler et al., *Scanning and Rotating Micromirrors Using Thermal Actuators*; Spie, vol. 3131, 1997, pp. 134-144.

(Continued)

*Primary Examiner*—James Phan
(74) *Attorney, Agent, or Firm*—Myers Bigel Sibley & Sajovec

(57) ABSTRACT

A disclosed scanner apparatus includes a member having spaced apart proximal and distal portions. An electromagnetic radiation device is configured to direct electromagnetic radiation therefrom and is moveably coupled to the distal portion of the member. The electromagnetic radiation device is configured to move in a first plane of movement to a first position to direct the electromagnetic radiation along a first path and configured to move in the plane of movement to a second position to direct the electromagnetic radiation along a second path. A MicroElectroMechanical Systems (MEMS) actuator is coupled to the electromagnetic radiation device, wherein the MEMS actuator is configured to move in a first direction to move the electromagnetic radiation device to the first position and configured to move in a second direction to move the electromagnetic radiation device to the second position. Other scanning and robotic structure devices are disclosed.

26 Claims, 19 Drawing Sheets

U.S. PATENT DOCUMENTS

| | | | |
|---|---|---|---|
| 5,206,557 A | 4/1993 | Bobbio | 310/309 |
| 5,321,501 A | 6/1994 | Swanson et al. | 356/345 |
| 5,781,333 A | 7/1998 | Lanzillotta et al. | 359/316 |
| 5,909,078 A | 6/1999 | Wood et al. | 310/307 |
| 5,945,898 A | 8/1999 | Judy et al. | 345/78 |

FOREIGN PATENT DOCUMENTS

| | | |
|---|---|---|
| GB | 2175705 A | 12/1986 |
| JP | 06160750 | 6/1994 |
| WO | WO/9321553 | 10/1993 |
| WO | WO98/09289 | 3/1998 |
| WO | WO/9835258 | 8/1998 |

OTHER PUBLICATIONS

Cowan et al., *Vertical Thermal Actuators for Micro-Opto-Electro-Mechanical Systems*, Spie, vol. 3226, 1997, pp. 137-146.

Fukuda et al., *Steering Mechanism and Swimming Experiment of Micro Mobile Robot in Water*; IEEE, vol. Workshop 8; Jan. 29, 1995; pp. 300-305.

Yamaguchi et al., *Distributed Electrostatic Micro Actuator*; IEEE, vol. Workshop 6, Feb. 7, 1993, pp. 18-23.

Riza et al.; *Micromechanical Fiber-Optic Switches for Optical Networks*: Spie, vol. 1793, Sep. 8, 1992, pp. 108-126.

Zara et al, *Intracardiac Ultrasound Scanner Using a Micromachine (MEMS) Actuator*, IEEE, vol. 47, No. 4, Jul. 2000, pp. 984-993.

International Search Report; Sep. 19, 2002; PCT/US01/28765.

K.L Gentry et al, *Optical Scanner Using a Micromachine (MEMS) Actuator*; Optical Society of America/SPIE Opto Southeast, Charlotte, North Carolina; Sep. 19, 2000.

SCANNER APPARATUS HAVING ELECTROMAGNETIC RADIATION DEVICES COUPLED TO MEMS ACTUATORS

CLAIM FOR PRIORITY

This application claims priority to U.S. Provisional Patent Application No. 60/233,262, filed on Sep. 18, 2000, by Smith et al., entitled Apparatus for Producing Forward-Looking Angular & Transverse Optical Scans, the entire disclosure of which is hereby incorporated herein by reference in its entirety.

STATEMENT OF GOVERNMENT SUPPORT

This invention was made with U.S. Government support under grant number HL-58754 from the National Institute of Health. The U.S. Government has certain rights to this invention.

FIELD OF THE INVENTION

The present invention relates to scanner devices in general, and more particularly, to electromagnetic radiation scanner devices.

BACKGROUND OF THE INVENTION

It is known in some industrial, medical, and consumer applications to scan objects. For example, U.S. Pat. No. 5,321,501 to Swanson et al. entitled Method and Apparatus for Optical Imaging with Means for Controlling the Longitudinal Range of the Sample, describes an assembly that scans angularly and transversely as shown in FIGS. 4A and 4B therein. As discussed in Swanson, the mechanism (107) that provides the scanning motion can be a piezoelectric crystal, a stepper motor, an electromagnetic actuator, or an electrostatic actuator. Some of these scanning mechanism may have control problems. For example, the oscillatory response of a piezoelectric crystal may suffer from hysteresis. Stepper motors can be large and consume significant power. Electromagnetic actuators may not be easily made in small sizes.

Scanners may also be utilized in biomedical areas. Some applications in the biomedical area include corneal resurfacing, optical imaging, and hair and tattoo removal. It is known to use galvanometers and other resonant scanners to steer optical beams in these types of biomedical applications. While galvanometers may offer a range of scan speeds and scan angles, galvanometers may require large magnetic bases and mirrors having relatively large masses to achieve desirable performance characteristics.

It is also known to fabricate scanners on silicon wafers using polysilicon as a substrate. It is also known to use electrostatic forces (amplified using comb drives), magnetic fields, thermal bending of bimorph cantilevers, and piezoelectric actuation to move mirrors in such scanners. These scanners can produce optical scan angles of about 7 to 180 degrees at frequencies from 40 Hz to 34 kHz using voltages in a range from 20 volts to 171 volts.

SUMMARY OF THE INVENTION

Embodiments according to the present invention can provide scanner devices. Pursuant to these embodiments, a member can have spaced apart proximal and distal portions. An electromagnetic radiation device can be configured to direct electromagnetic radiation therefrom and can be moveably coupled to the distal portion of the member. The electromagnetic radiation device can be configured to move in a first plane of movement to a first position to direct the electromagnetic radiation along a first path and configured to move in the plane of movement to a second position to direct the electromagnetic radiation along a second path. A MicroElectroMechanical Systems (MEMS) actuator can be coupled to the electromagnetic radiation device, wherein the MEMS actuator can be configured to move in a first direction to move the electromagnetic radiation device to the first position and configured to move in a second direction to move the electromagnetic radiation device to the second position.

DETAILED DESCRIPTION OF EMBODIMENTS ACCORDING TO THE INVENTION

The invention now will be described more fully hereinafter with reference to the accompanying drawings, in which embodiments of the invention are shown. The invention may, however, be embodied in many different forms and should not be construed as limited to the embodiments set forth herein; rather, the embodiments are provided so that this disclosure will be thorough and complete, and will fully convey the scope of the invention to those skilled in the art. Like numbers refer to like elements throughout.

It will be understood that when an element such as a layer, region or substrate is described as being "on" another element, it can be directly on the other element or intervening elements may also be present. In contrast, when an element is described as being "directly on" another element, there are no intervening elements present It will also be understood that when an element such as a member, frame, hinge, electromagnetic radiation device, or MicroElectroMechanical Systems (MEMS) actuator is described as being "coupled to" another element, it can be directly coupled to the other element or intervening elements may also be present.

As used herein, the term "electromagnetic radiation" can include radiation that can be used to transmit or direct information in a system, such as radiation in the visible, ultraviolet, infrared and/or other portions of the electromagnetic radiation spectrum. The power of the electromagnetic radiation can vary based on the application. For example, some embodiments according to the present invention use relatively high power lasers to generate the electromagnetic radiation.

As used herein the term "electromagnetic radiation device" can include any device which is capable of providing electromagnetic radiation therefrom, such as a reflector or mirror, or a device which generates electromagnetic radiation, such as a camera, or a device that allows electromagnetic radiation to pass therethrough, such as a lens or the like. Accordingly, it will be understood that the electromagnetic radiation devices described herein do not necessarily generate the electromagnetic radiation, but can instead reflect, focus, or otherwise direct the electromagnetic radiation along different paths to achieve a result, such as to direct information or therapy.

As used herein the term "hinge" is defined to mean a device that allows two elements, coupled thereto, to pivot in a plane of movement. For example, in some embodiments according to the present invention, the hinge can be a flexible material, an end of which may move in a direction in which an element coupled thereto is pivoted. The hinge can allow repeated pivoting of the elements over an extended duration.

Figure 1:
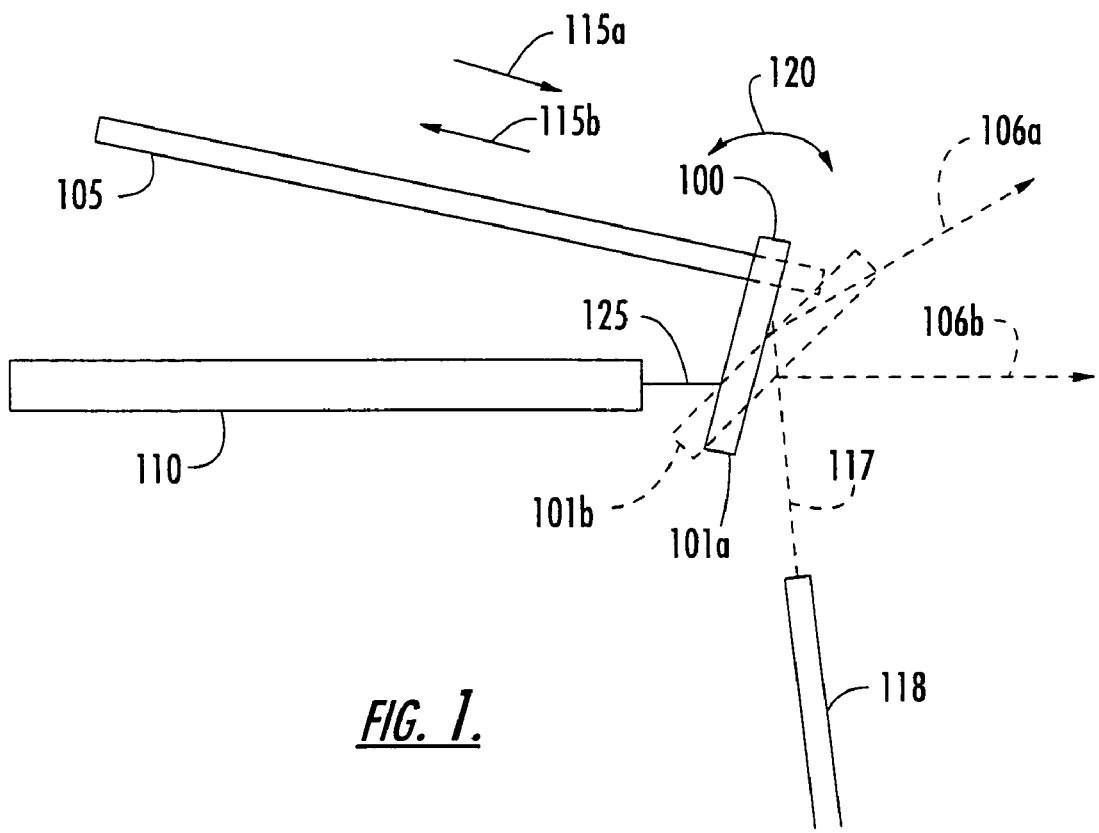
FIGS. 1 to 4 are schematic diagrams that illustrate scanner devices according to embodiments of the present invention.

FIG. 1 is a schematic diagram that illustrates scanner devices according to embodiments of the present invention. A proximal portion of a member 110 is movably coupled to a first portion of an electromagnetic radiation device 100 by a hinge 125. In some embodiments according to the present invention, the member 110 is made from a polyimide material. An integrated force array actuator (IFA) 105 is coupled to the electromagnetic radiation device 100 at a second portion thereof that is spaced apart from the first portion. The IFA 105 is configured to expand and contract, in directions 115$a$ and 115$b$ respectively, to pivot the electromagnetic radiation device 100 in a plane of movement 120 about the hinge 125.

The IFA 105 can be used to pivot the electromagnetic radiation device 100 about the hinge 125 to direct electromagnetic radiation 117 incident thereon along different paths. For example, when the IFA 105 contracts in the direction 115$b$, the electromagnetic radiation device 100 pivots in the plane of movement 120 to a first position 101$a$ to reflect the electromagnetic radiation 117 from a source 118 along a first path 106$a$. When the IFA 105 expands in the second direction 115$a$, the electromagnetic radiation device 100 pivots on the hinge 125 in the plane of movement 120 to a second position 101$b$ to reflect the electromagnetic radiation 117 along a second path 106$b$. Accordingly, embodiments of scanner devices according to the present invention can be used to scan electromagnetic radiation in the plane of movement 120.

In some embodiments according to the present invention, the IFA 105 is movably coupled to the electromagnetic radiation device 100 by a second hinge (not shown) so that the expansion and contraction of the IFA 105 can be translated into the plane of movement 120. In some embodiments according to the present invention, the electromagnetic radiation 117 defines a different angle with the electromagnetic radiation device 100 than the one shown in FIG. 1.

Figure 2:
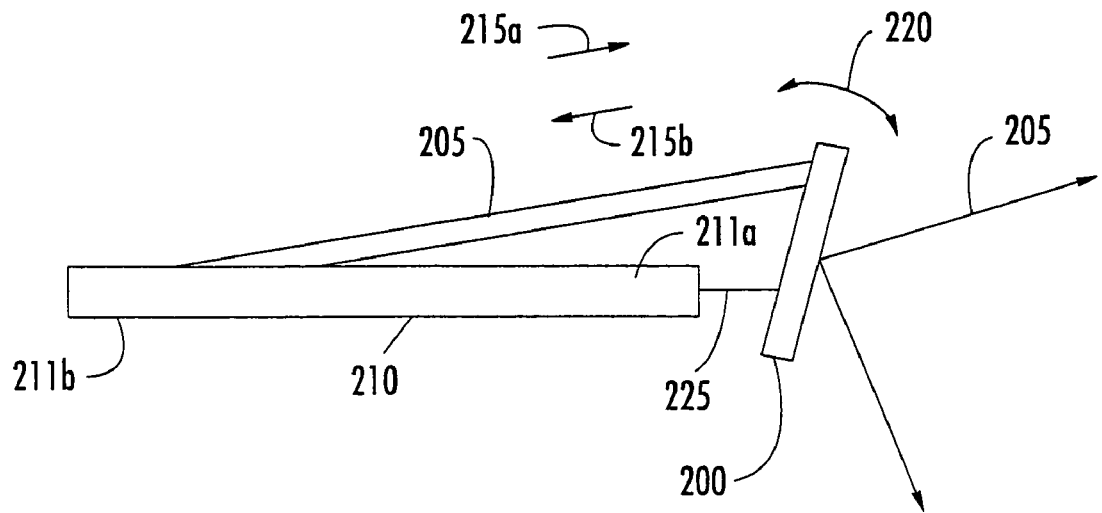

FIG. 2 is a schematic diagram that illustrates scanner devices according to embodiments of the present invention. As shown in FIG. 2, a distal end of an IFA 205 is coupled to a distal portion 211$b$ of a member 210 and a proximal end of the IFA 205 is coupled to an electromagnetic radiation device 200. The electromagnetic radiation device 200 is moveably coupled to a proximal portion 211$a$ of the member 210 via a hinge 225. The IFA 205 is configured to expand and contract in first and second directions 215$a$ and 215$b$ to pivot the electromagnetic radiation device 200 in a plane of movement 220 about the hinge 225 to direct electromagnetic radiation incident thereon along different paths.

Figure 3:
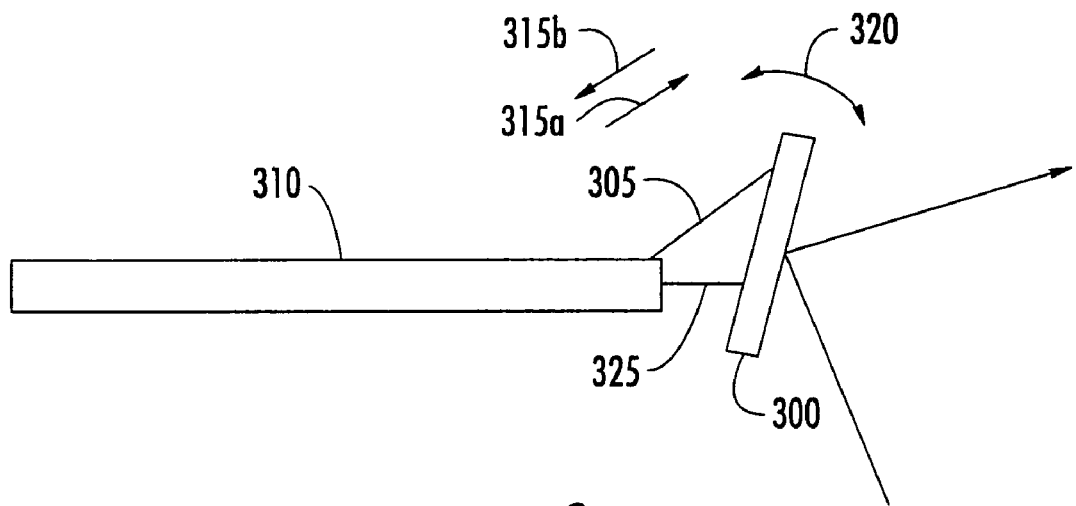

FIG. 3 is a schematic diagram that illustrates scanner devices according to embodiments of the present invention. As shown in FIG. 3, an IFA 305 is connected to a proximal portion of a member 310 and to an electromagnetic device 300. The IFA 305 is configured to expand and contract in first and second directions 315$a$, 315$b$ to pivot the electromagnetic radiation device 300 in a plane of movement 320 about a hinge 325 that moveably couples the electromagnetic radiation device 300 to the proximal portion of the member 310 to direct electromagnetic radiation along different paths. As shown in FIG. 3, the points where the IFA 305 and the hinge 325 are coupled to the electromagnetic radiation device 300 are spaced apart from one another.

Figure 4:
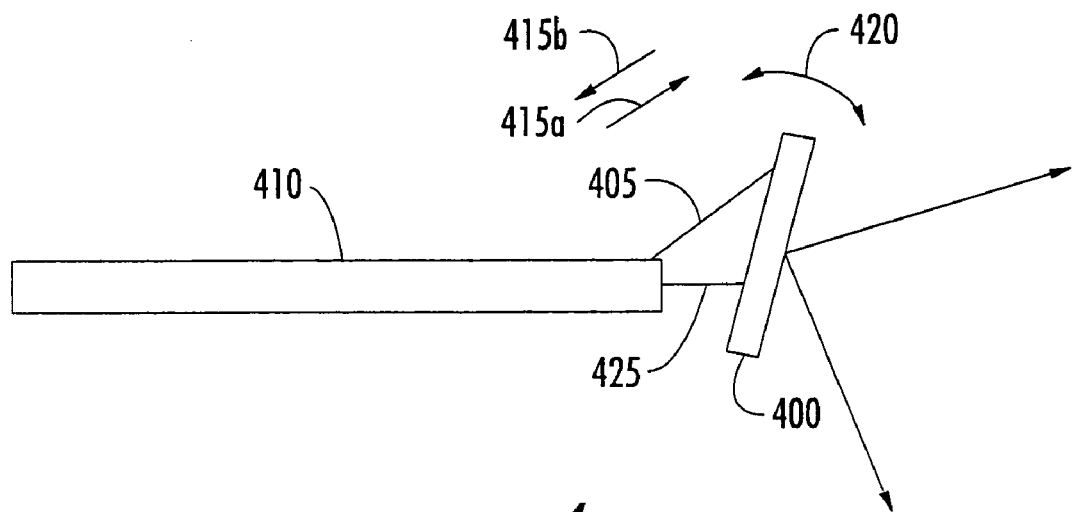

FIG. 4 is a schematic diagram that illustrates embodiments of scanner devices according to the present invention. As shown in FIG. 4, the points where an IFA 405 and a hinge 425 are coupled to an electromagnetic radiation device 400 can be spaced closer together in comparison to those shown in FIG. 3. A member 410 is moveably coupled to the electromagnetic radiation device 400 by the hinge 425. A distal end of the IFA 405 is coupled to a proximal portion of the member 400. The IFA 405 is configured to expand and contract in directions 415a and 415b respectively to pivot the electromagnetic radiation device 400 in a plane of movement 420 about the hinge 425 to direct electromagnetic radiation along different paths.

In some embodiments according to the present invention, the IFAs are MEMS based actuators such as those disclosed in U.S. Pat. No. 5,206,557 to Bobbio entitled Microelectromechanical Transducer and Fabrication Method, the disclosure of which is hereby incorporated herein by reference. As discussed in Bobbio, an IFA is a network of micron-scaled deformable capacitive cells that include capacitor electrodes. The capacitive cells can contract due to an electrostatic force produced by a differential voltage applied across the capacitor electrodes. The electrostatic force produced by a capacitive cell with polyamide electrodes and a dielectric of air is given as follows:

$$F = \frac{\varepsilon A V^2}{1.2 L^2} \quad (1)$$

where F is the electrostatic force produced, A is the surface area of the capacitor plate, V is the applied voltage, $\varepsilon$ is the dielectric constant of air, and L is the capacitor electrode separation.

Figure 5A:
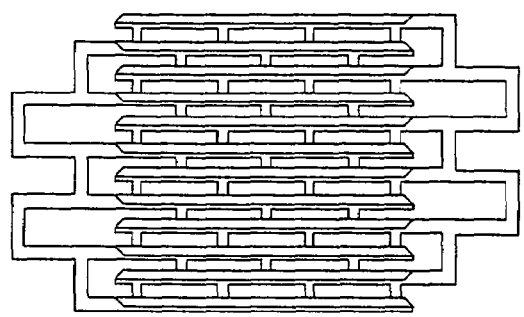
FIGS. 5a and 5c are schematic diagrams that illustrate integrated force array actuators in a relaxed state and in a contracted state respectively.
Figure 5B:
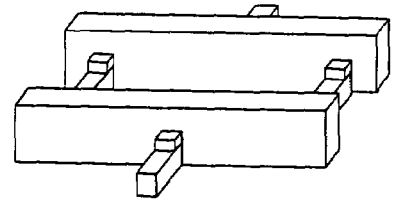
FIGS. 5b and 5d are perspective views that illustrate single cells of an integrated force array actuator in a relaxed state and in a contracted state respectively.
Figure 5C:
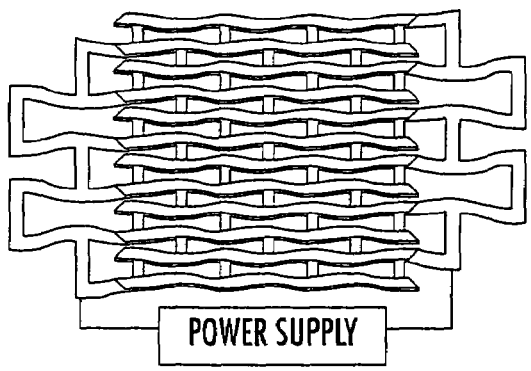
Figure 5D:
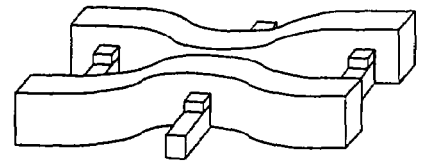

As shown in FIGS. 5A and 5B, when the capacitive cells are in a relaxed state, the spacing between the plates of the capacitive cells are at a first distance. As shown in FIGS. 5C and 5D, when a voltage is applied across the plates of the capacitive cells, the plates are deformed by the electrostatic force between the plates, thereby causing the IFA to contract along its length. Accordingly, when a voltage is applied to the IFA, the IFA contracts to reduce its length compared to when the IFA is in the relaxed state.

It will be understood that other types of MEMS actuators can be used. For example, in some embodiments according to the present invention, a Thermal Arched Beam (TAB) actuator is used to pivot the electromagnetic radiation device about the hinge. TABs are further described in U.S. Pat. No. 5,909,078 entitled Thermal Arched Beam Microelectromechanical Actuators to Wood et al., the disclosure of which is hereby incorporated herein by reference.

Figure 6A:
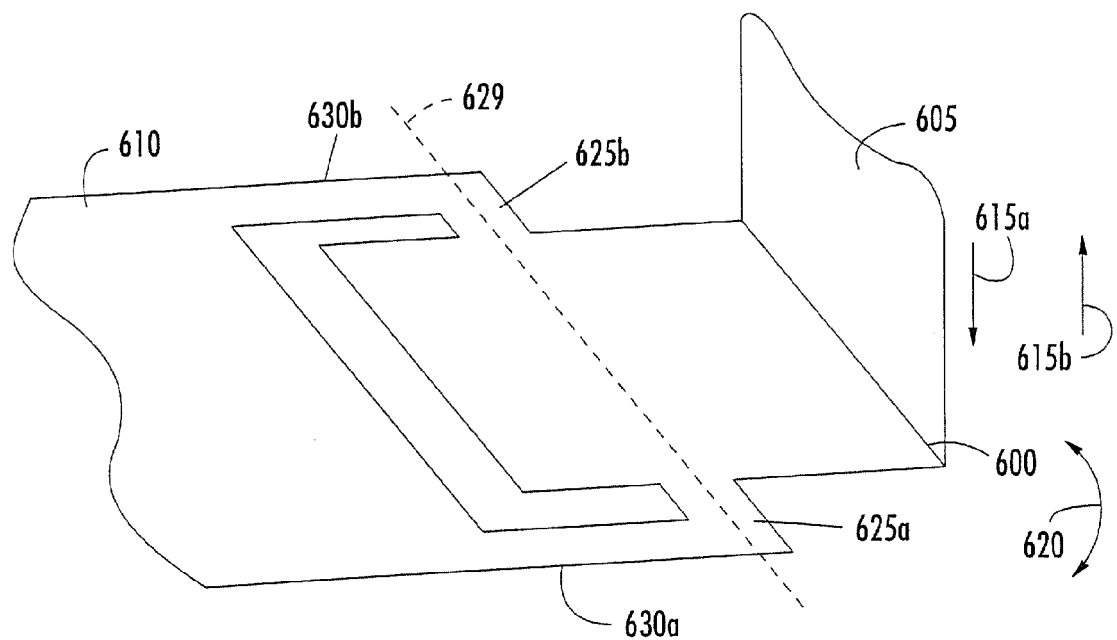
FIGS. 6a and 6b are schematic diagrams that illustrate electromagnetic radiation device, and integrated force array actuators according to embodiments of the present invention.

FIG. 6A is a perspective view that illustrates embodiments of an electromagnetic radiation device 600. A member 610 is coupled to a frame having first and second opposing portions 630a-b. The first opposing portion of the frame 630a is moveably coupled to the electromagnetic radiation device 600 by a first hinge 625a. The second opposing portion of the frame 630b is moveably coupled to the electromagnetic radiation device 600 by a second hinge 625b. The first and second hinges 625a-b define an axis 629 therethrough Although the frames are shown in depicted as rectangular square in the figures, it will be understood that other shapes, such as circular or elliptical, may be used for the frames.

Figure 6B:
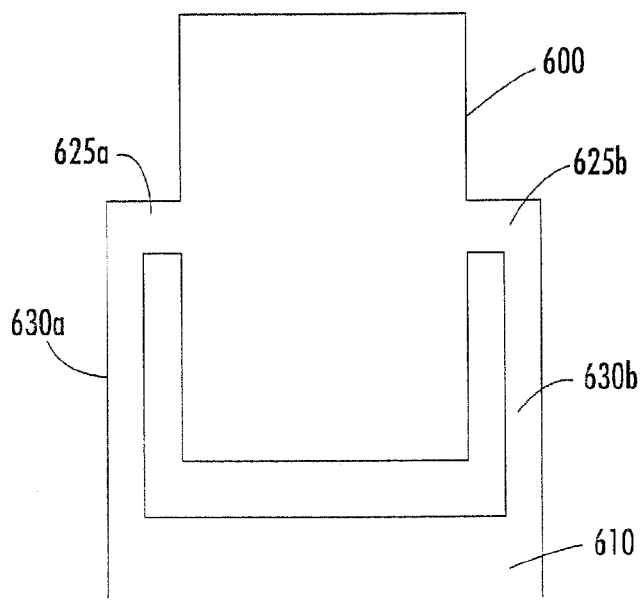

An IFA 605 is coupled to a point on the electromagnetic radiation device 600 which is spaced apart from the axis 629 and is configured to expand and contract in directions 615a and 615b respectively to pivot the electromagnetic radiation device 600 in a plane of movement 620 about the axis 629. Accordingly, the IFA 605 can be used to direct electromagnetic radiation therefrom along different paths. FIG. 6B is a top view of the electromagnetic device 600 shown in FIG. 6A.

In some embodiments according to the present invention, the hinges can be torsion type hinges having a rectangular shape that are configured to be subjected to a twisting torque applied by the expansion and contraction of the IFA coupled to the electromagnetic radiation device. In some embodiments according to the present invention, the hinges have dimensions of approximately 60 microns by 250 microns by about 3 microns thick. In some embodiments according to the present invention, the hinges are made of polyimide. The angular displacement of the hinges can be approximated by the following formulas:

$$\Theta(l) = \frac{Tl}{2(1-\mu)Dc}\left(\frac{\tanh(4\lambda)}{4\lambda}\right) \quad (2)$$

$$\lambda = \frac{l}{c}\sqrt{1.5(1-\mu)} \quad (3)$$

$$D = \frac{Eh^3}{12(1-\mu^2)} \quad (4)$$

in Equation (2) $\lambda$ is an aspect ratio parameter that is provided by Equation (3) in which l is the length of the hinge which can be, for example, 250 microns, c is the hinge width which can be, for example, 60 microns, $\mu$ is Poisson's ratio for polyimide which is about 0.34, D is a local flexion stiffness that is described by Equation (4), where E is the elastic modulus of polyimide, which can be about 2600 Mpa, and h is the hinge thickness which can be about 3 microns.

The angular displacement determined using Equation (2) can be used to determine a torsion constant that can be used to relate the applied moment to an angular displacement. The torsion constant, k, can be used to determine the resonant frequencies of the structure in air using the following equation:

$$f = \frac{1}{2\pi}\sqrt{\frac{k}{I}} \quad (5)$$

Figure 7:
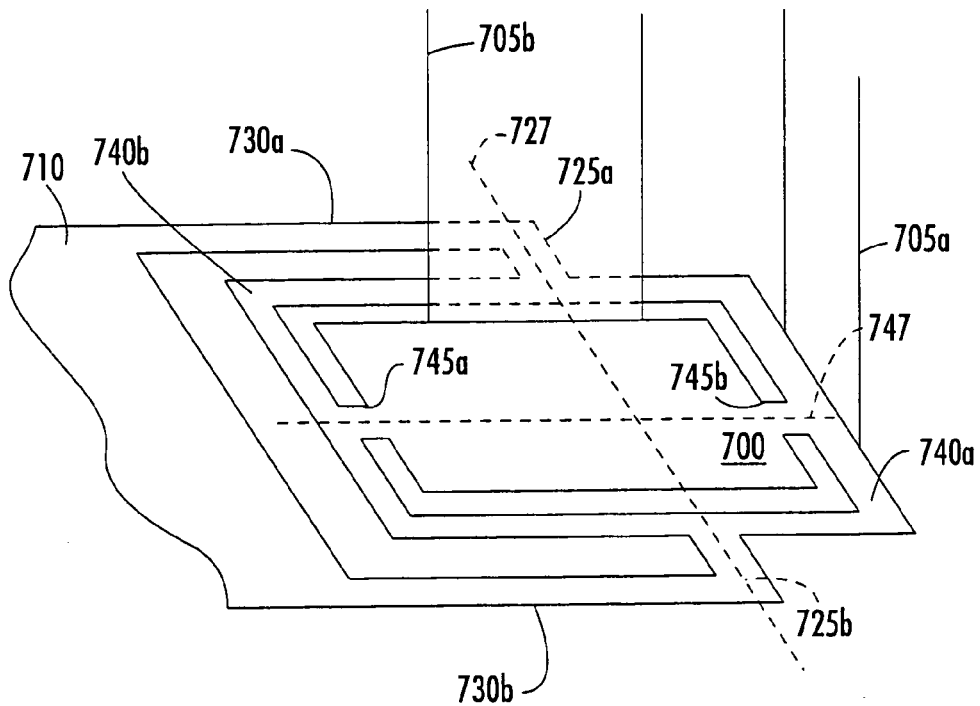
FIG. 7 is a perspective view that illustrates electromagnetic radiation devices configured to pivot in two planes of movement according to embodiments of the present invention.

FIG. 7 is a perspective view that illustrates embodiments of an electromagnetic radiation 700 device in a Cardano type suspension according to the present invention. As shown in FIG. 7, a first frame includes first and second opposing portions 730a, 730b that are coupled to a member 710. First and second hinges 725a, 725b are coupled to the first and second opposing portions of the frame 730a, 730b and define a first axis 727 therethrough. A second frame is located in an interior portion of the first frame and includes first and second opposing portions 740a, 740b. A third hinge 745a is coupled to the first opposing portion 740b of the second frame and a fourth hinge 745b is coupled to the second opposing portion 740a of the second frame. The third and fourth hinges 745a-b moveably couple the second frame to the electromagnetic radiation device 700 located in the interior region of the second frame. The third and fourth hinges 745a-b define a second axis 747 therethrough about which the electromagnetic radiation device 700 pivots. The electromagnetic radiation device 700 also pivots about the first axis 727. In particular, a first IFA 705a is coupled to the second frame and is configured to expand and contract to pivot the second frame and the electromagnetic radiation device 700 about the first axis 727. A second IFA 705b is coupled to the electromagnetic radiation device 700 and is configured to pivot the electromagnetic radiation device 700 about the second axis 747. Accordingly, the first and second IFAs 705a-b pivot the electromagnetic radiation device 700 in two planes of movement, the first plane of movement being about the first axis 727, and the second plane of movement being about the second axis 747.

As discussed above, embodiments of electromagnetic radiation devices according to the present invention can direct electromagnetic radiation along different paths, generate electromagnetic radiation, focus the electromagnetic radiation, and the like. For example, in embodiments according to the present invention having electromagnetic radiation devices that reflect electromagnetic radiation, the electromagnetic radiation device can be a reflector or mirror. The reflector can be made a metal, such as gold.

Figure 8:
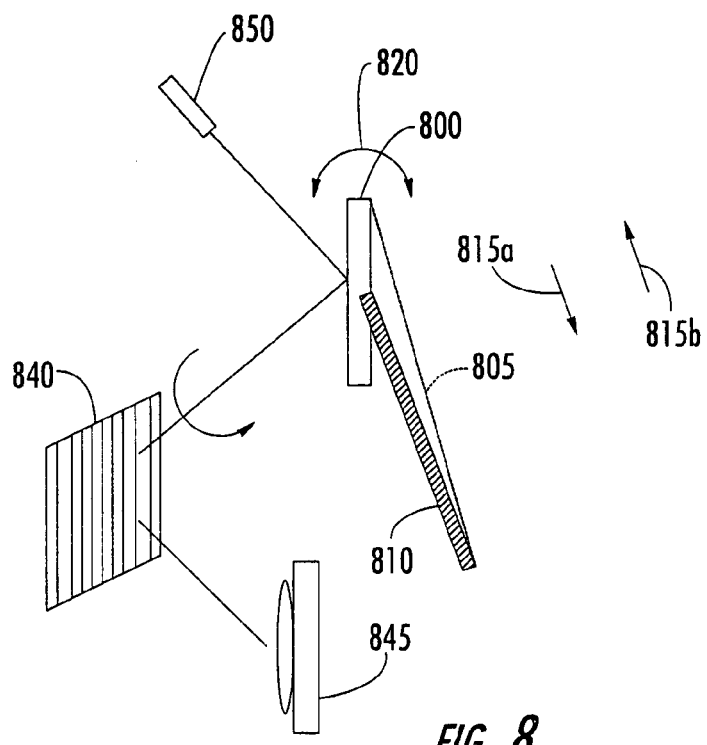
FIG. 8 is a schematic diagram that illustrates optical barcode scanners according to embodiments of the present invention.

For example, FIG. 8 is a schematic diagram that illustrates scanning devices including reflectors according to embodiments of the present invention. In particular, the reflector can be used as part of an optical barcode scanner wherein a helium neon laser 850 projects laser light onto a reflector 800. The reflector 800 is moveably coupled to a member 810 by at least one hinge which is not shown. The reflector 800 is configured to pivot about the at least one hinge in a plane of movement 820. A distal end of an IFA 805 is coupled to a distal end of the member 810. A proximal end of the IFA 805 is coupled to the reflector 800. The IFA 805 is configured to contract and expand in directions 815a and 815b respectively to pivot the reflector 800 in the plane of movement 820 to scan the electromagnetic radiation across a barcode 840 which is reflected to a photo detector 845. The photo detector 845 can determine the configuration of the barcode 840 based on the reflected energy therefrom.

In further embodiments according to the present invention, electromagnetic radiation can be used to scan a body to assist in the diagnosis of skin conditions, such as skin cancer. In other embodiments according to the present invention, electromagnetic radiation can be used to scan a body to provide body dimensions for the sizing of garments. In other embodiments according to the present invention, electromagnetic radiation can be used to direct light for light displays or light shows.

Figure 9:
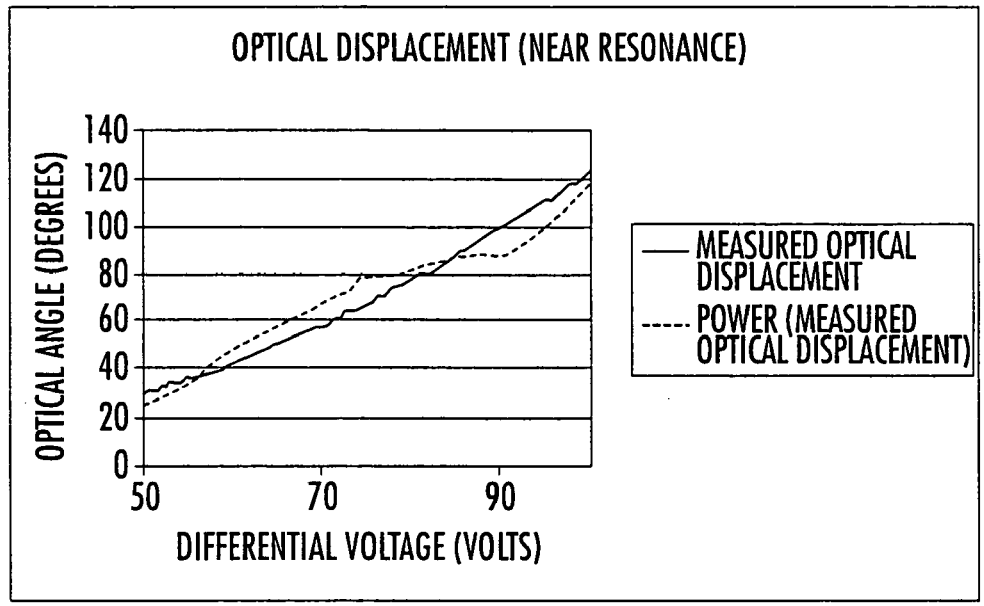
FIG. 9 is a graph that illustrates optical angular displacement as a function of voltage according to embodiments of the present invention.
Figure 10:
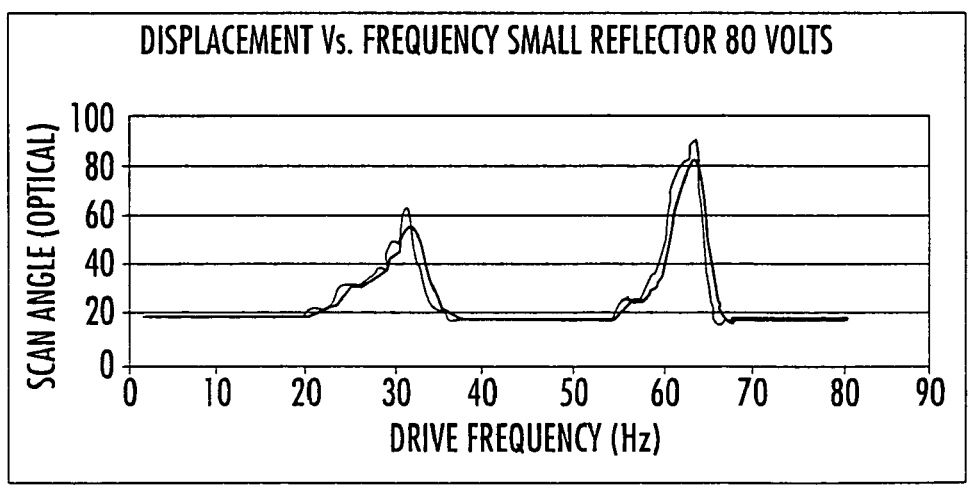
FIG. 10 is a graph that illustrates optical angular displacement as a function of frequency according to embodiments of the present invention.

FIG. 9 is an exemplary graph that illustrates optical angular displacement as a function of the voltage applied to an IFA according to the present invention. In particular, as the voltage increases, the angle over which the reflector is displaced increases. FIG. 10 is an exemplary graph that illustrates angular displacement as a function of a frequency associated with the voltage applied to the IFA. In particular, FIG. 10 shows that, according to some embodiments of the present invention, pronounced angular displacement can be achieved near a resonant frequency associated with the system. FIG. 10 also shows that resonance can be achieved at about 60 Hz while lesser displacements can be achieved at near a resonant frequency of about 30 Hz.

Figure 11A:
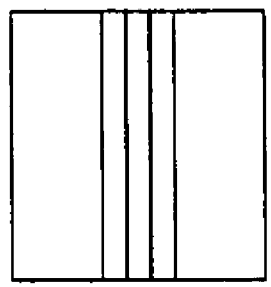
FIG. 11A is an exemplary barcode scanned by an optical bar code scanner according to embodiments of the present invention.
Figure 11B:
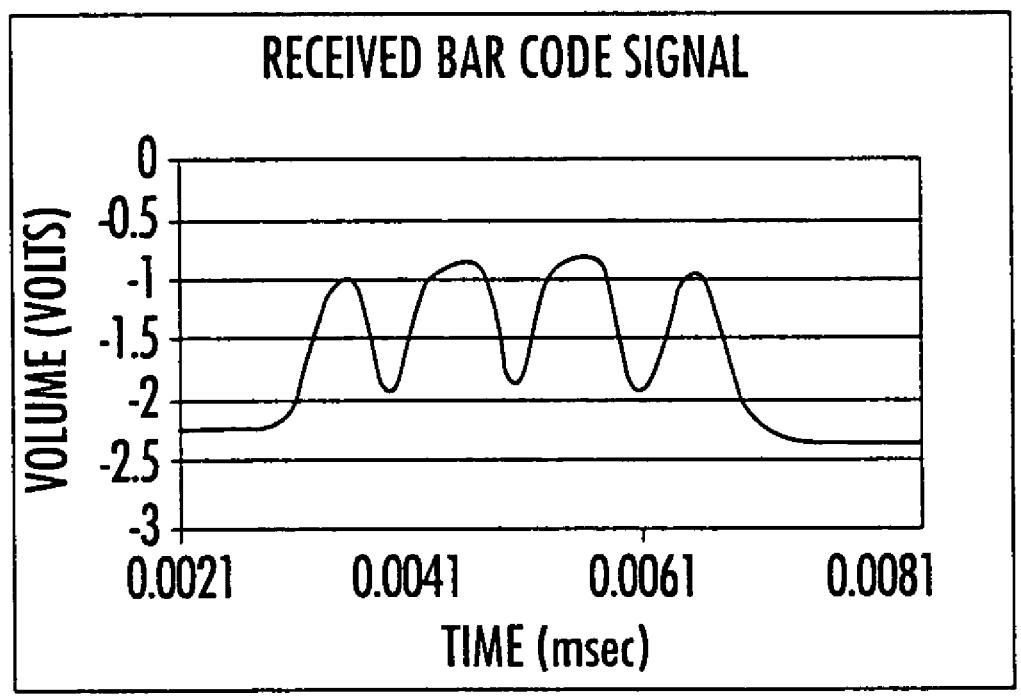
FIG. 11B is a graph of a signal produced by an optical bar code scanner scanning the barcode of FIG. 11A according to embodiments of the present invention.
Figure 12:
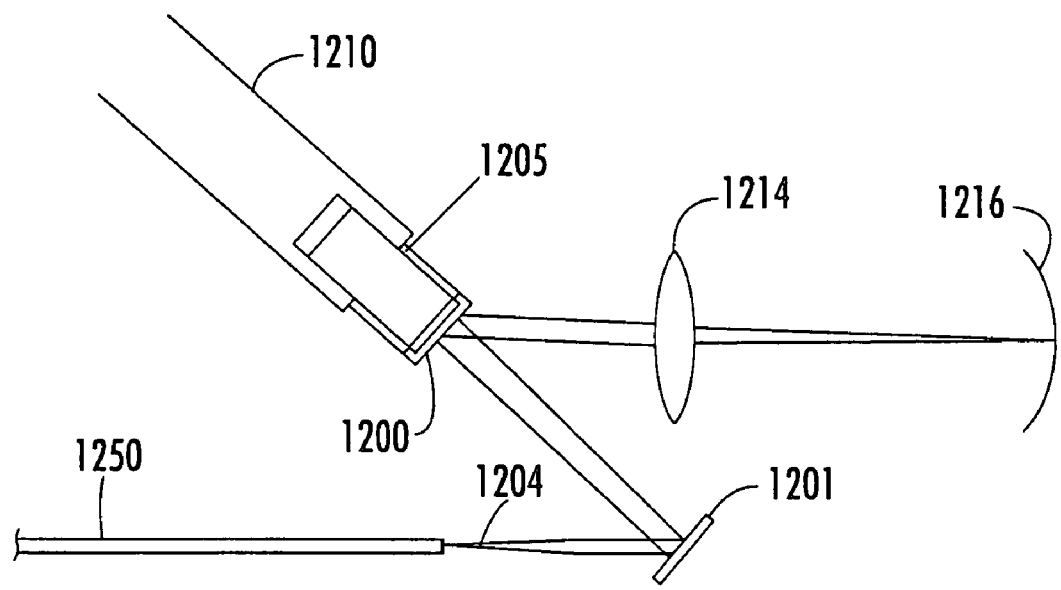
FIG. 12 is a schematic diagram that illustrates optical scanner systems according to embodiments of the present invention.

FIG. 11A is an exemplary barcode scanned by the optical barcode scanning system illustrated in FIG. 8. FIG. 11A is an exemplary graph that illustrates a response of the photo detector 845 based on the laser light scanned across the barcode in FIG. 11A. As shown in FIG. 11A, localized peaks of the voltage signal can be associated with lighter areas of the barcode where increased laser light is received by the photodetector 845. Conversely, the localized minima of the voltage signal can be associated with the dark bands in the exemplary barcode of FIG. 11A FIG. 12 is a schematic diagram that illustrates optical scanning systems according to embodiments of the present invention. In particular, an electromagnetic radiation source 1250 directs electromagnetic radiation 1204 to a first reflector 1201 which reflects that electromagnetic radiation 1204 to a second reflector 1200 according to the present invention. The second reflector 1200 is coupled to an IFA 1205 that is configured to expand and contract to pivot the second reflector 1200 to reflect the electromagnetic radiation through a lens 1214 which focuses the electromagnetic radiation onto a sample 1216.

Figure 13:
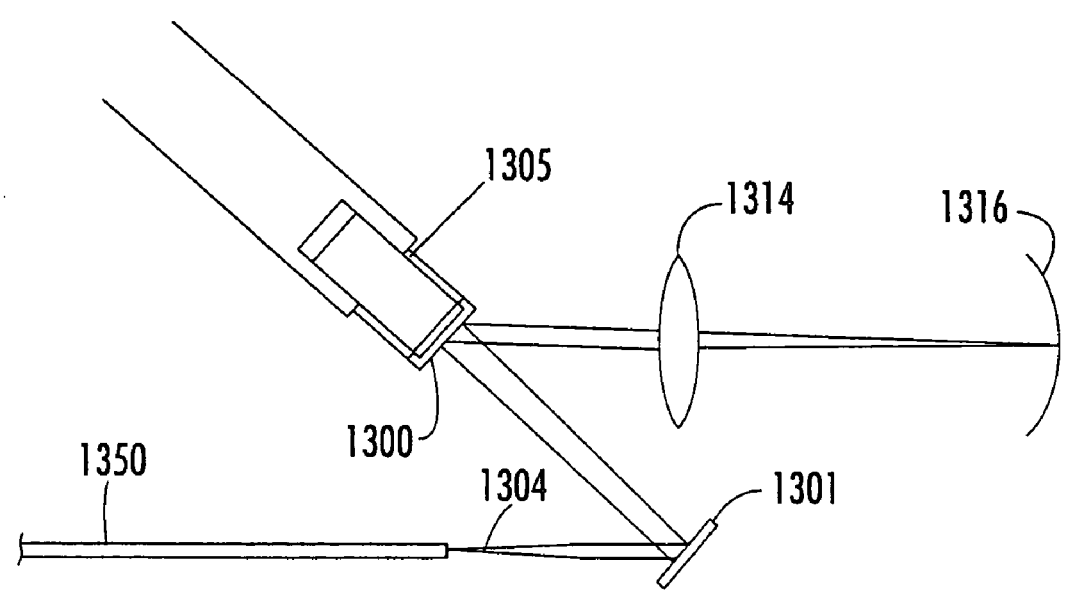
FIG. 13 is a schematic diagram that illustrates optical scanner systems according to embodiments of the present invention.

FIG. 13 is a schematic diagram that illustrates optical scanning systems according to embodiments of the present invention. In particular, an electromagnetic radiation source 1350 generates electromagnetic radiation 1304 which is reflected by a first reflector 1301 to a second reflector 1300. The second reflector 1300 is coupled to an IFA 1305 which is configured to pivot the second reflector 1300 about a hinge (which is not shown) to reflect the electromagnetic radiation to a lens 1314. The lens is coupled to a second IFA 1315 that is configured to move the lens 1314 towards and away from the second reflector 1300. The lens 1314 moves to focus the electromagnetic radiation from the second reflector 1300 onto a sample 1316.

Figure 14:
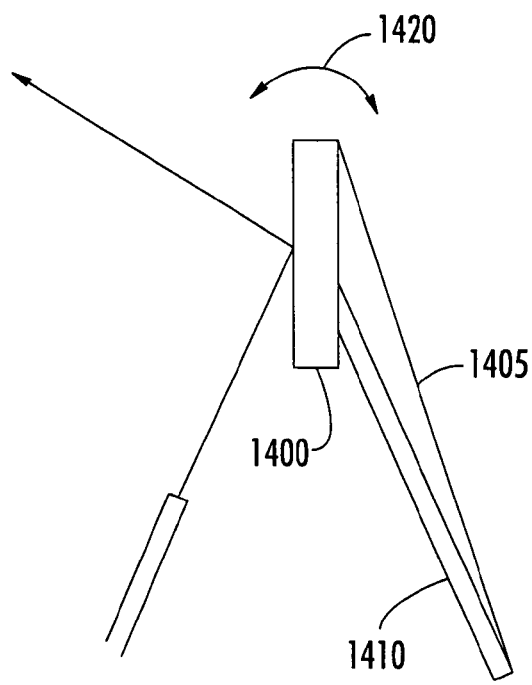
FIG. 14 is a schematic diagram that illustrates confocal microscope systems according to embodiments of the present invention.

FIG. 14 is a schematic diagram of a confocal microscope system according to the present invention. According to FIG. 14, the confocal microscope system can generate laser light which is reflected off a reflector 1400 to a tissue sample. As discussed above, the reflector 1400 is pivoted about hinges (not shown) by expansion and contraction of an IFA 1405 that is coupled to the reflector 1400. A lens (not shown) can be positioned along the path of the electromagnetic radiation to focus the laser light. Accordingly, the confocal microscope system according to the present invention shown in FIG. 14 can scan tissue to produce an image of a slice of the tissue.

Figure 15:
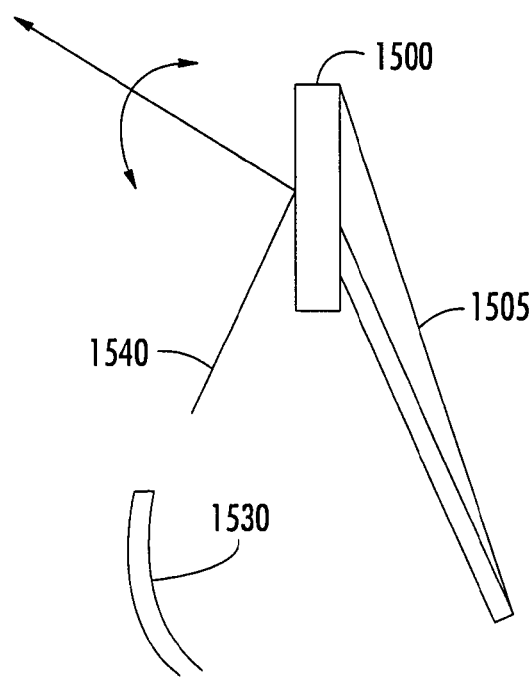
FIG. 15 is a schematic diagram that illustrates optical coherence tomography systems according to embodiments of the present invention.

FIG. 15 is a schematic diagram that illustrates optical coherence tomography systems (OCT) according to embodiments of the present invention. An OCT system is analogous to ultrasound in that light incident on the tissue is reflected therefrom and can be used to create a tomographic image of the tissue. According to FIG. 15, infrared light 1540 from an infrared light source 1530 is projected onto a reflector 1500 according to the present invention. The infrared light 1540 is scanned across the tissue by pivoting the reflector 1500 using an IFA 1505 as described above. The infrared light reflected from the tissue can be sampled to create a tomographic image.

Figure 16:
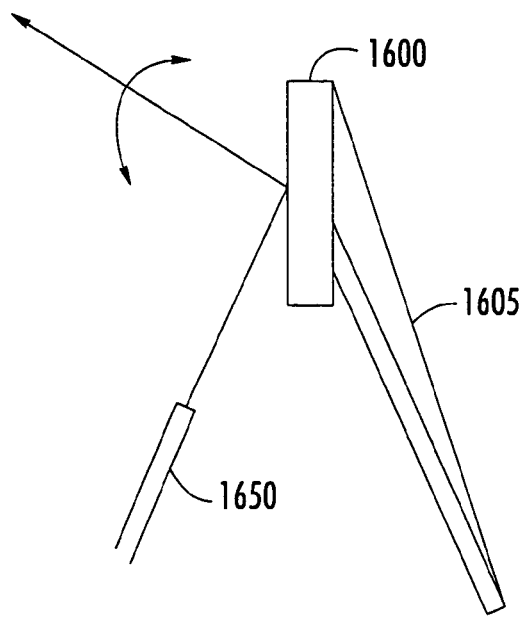
FIG. 16 is a schematic diagram that illustrates hair/tattoo removal systems according to embodiments of the present invention.

FIG. 16 is a schematic diagram that illustrates hair/tattoo removal systems according to embodiments of the present invention. According to FIG. 16, an alexandrite laser 1650 projects light onto a reflector 1600 according to the present invention. The reflector 1600 is pivoted about a set of hinges (not shown) by the expanding and contracting an IFA 1605 that is coupled thereto to scan the hair or tattoo to be removed.

Figure 17:
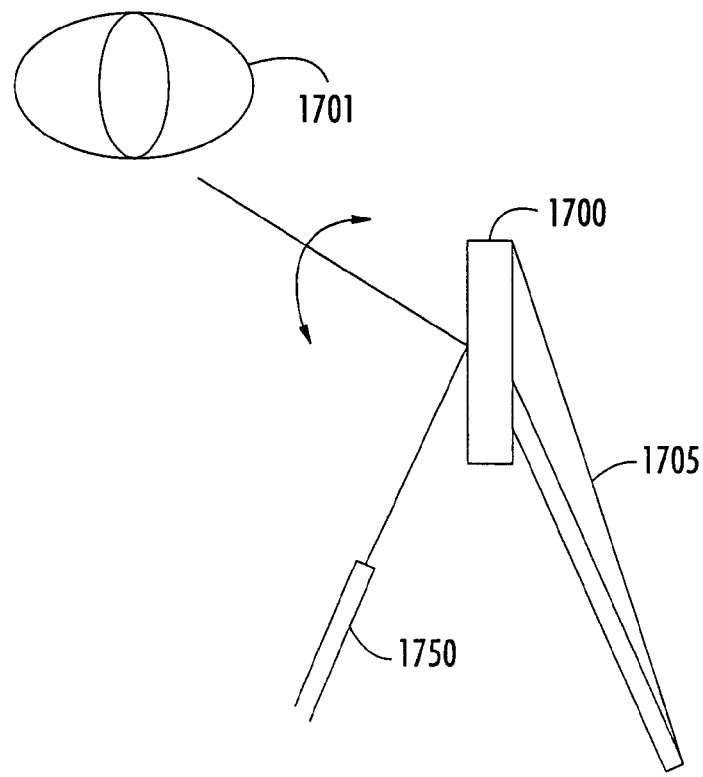
FIG. 17 is a schematic diagram that illustrates corneal resurfacing systems according to embodiments of the present invention.

FIG. 17 is a schematic diagram that illustrates corneal resurfacing systems according to embodiments of the present invention. According to FIG. 17, an ultraviolet radiation source 1750 generates ultraviolet radiation which is reflected off a reflector 1700 onto a corneal surface of an eye 1701. The reflector 1700 pivots about a hinge (not shown) when an IFA 1705 expands and contracts as discussed above. Scanning devices according to the present invention can therefore be used to scan ultraviolet radiation across a patient's eye to conduct laser eye surgery or the like. For example, the ultraviolet radiation can heat and reshape the cornea of the patient's eye to correct near and far sightedness.

Figure 18:
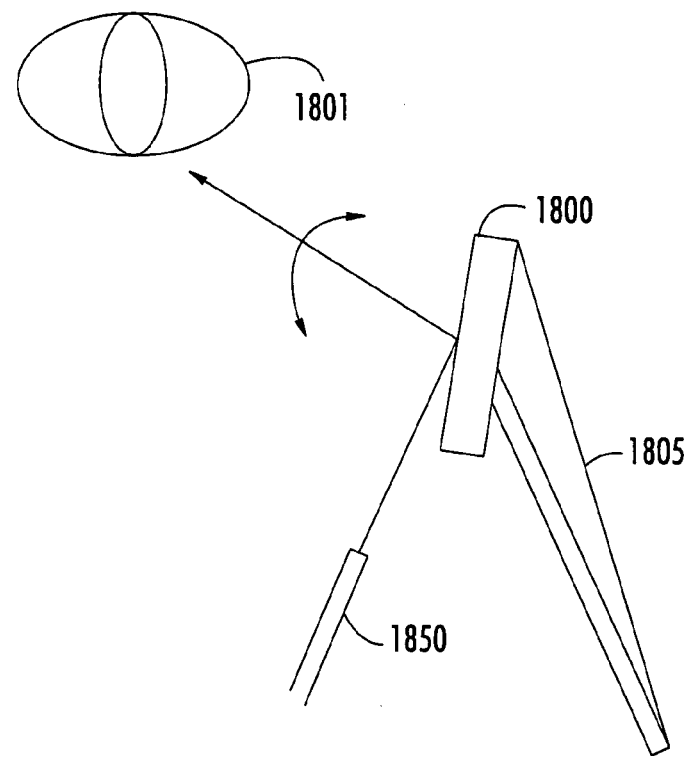
FIG. 18 is a schematic diagram that illustrates optical image projection systems according to embodiments of the present invention.

FIG. 18 is a schematic diagram that illustrates optical image systems according to embodiments of the present invention. According to FIG. 18, image data is projected from an image source 1850 to a reflector 1800 which reflects the image data onto a retina of a subject's eye 1801. The image is projected onto the retina by pivoting the reflector 1800 by expanding and contracting an IFA 1805 coupled thereto as discussed above.

Figure 19:
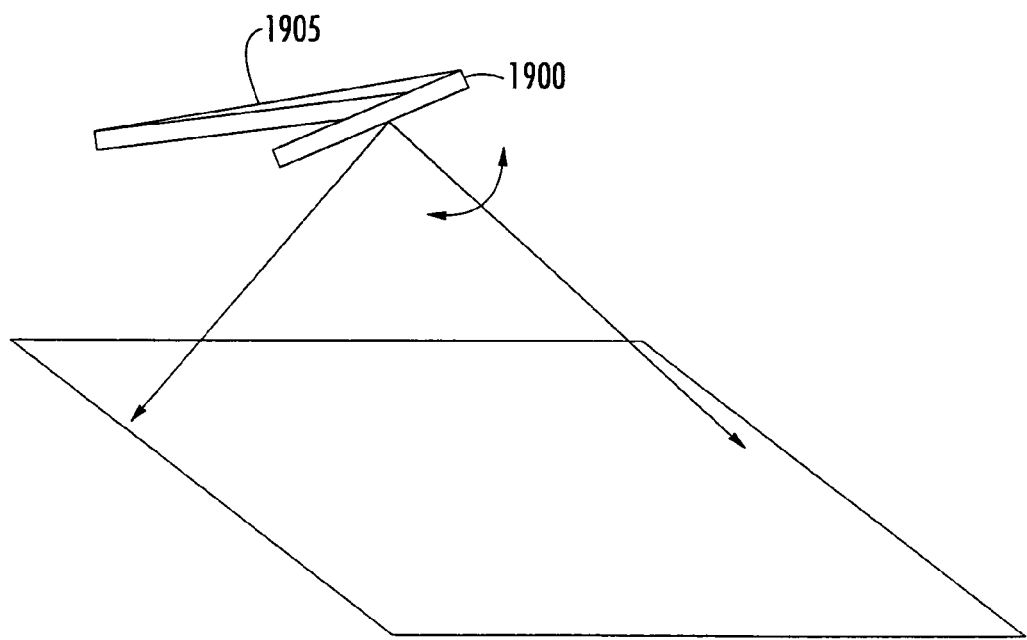
FIG. 19 is a schematic diagram that illustrates two dimensional optical text scanners according to embodiments of the present invention.

FIG. 19 is a schematic diagram that illustrates text scanners according to embodiments of the present invention. According to FIG. 19, an electromagnetic radiation source 1900 can be pivoted to scan text on a page 1901. For example, the scanning device of FIG. 19 can be implemented in a text reading pen which a user drags across the text to be scanned. In particular, the electromagnetic radiation source 1900 is configured to pivot out of plane relative to a direction in which the pen is dragged across the text. In further embodiments according to the present invention, the electromagnetic radiation source 1900 can be mounted in a Cardano type suspension, such as that discussed in relation to FIG. 7, so that the electromagnetic radiation source 1900 is configured to pivot in two dimensions to further reduce the time needed to scan text on the page 1901.

Figure 20:
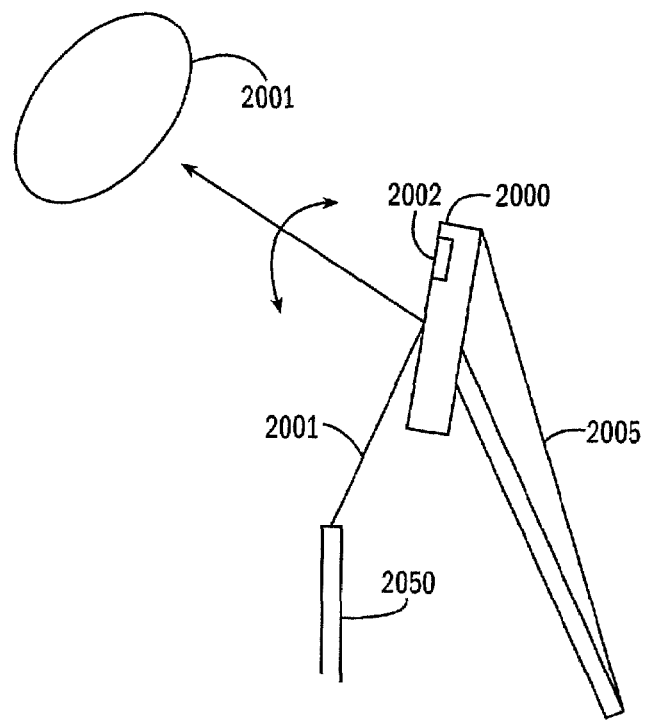
FIG. 20 is a schematic diagram that illustrates combined optical/2D ultrasound imaging system according to embodiments of the present invention.

FIG. 20 is a schematic diagram that illustrates a combined optical/ultrasound scanner according to the present invention. According to FIG. 20, an electromagnetic radiation source 2050 generates electromagnetic radiation 2021 which is reflected off a reflector 2000 onto a target 2001. An ultrasound transducer 2002 is mounted on the reflector 2000 and produces ultrasonic energy which can be used to scan the target 2001. When the reflector 2000 is pivoted by an IFA 2005, the electromagnetic radiation and the ultrasound energy can both be directed to the target 2001 thereby producing both imaging and ultrasound data corresponding to the target 2001.

Figure 21:
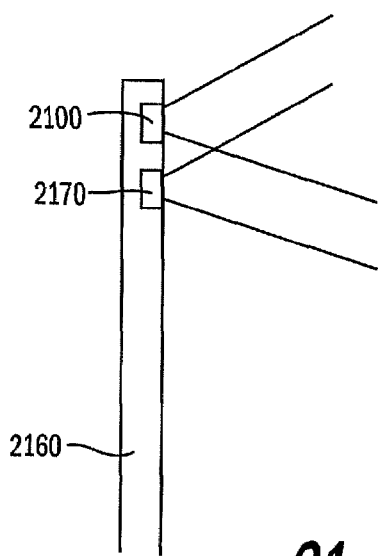
FIG. 21 is a schematic diagram that illustrates combined optical/ultrasound scanning catheters according to embodiments of the present invention.

FIG. 21 is a schematic diagram that illustrates combined OCT/ultrasound scanners in a catheter 2160. According to FIG. 21, a scanning device 2100 according to embodiments of the present invention can be embedded in the catheter 2160 and configured to scan tissue in which the catheter is placed by pivoting in response to expansion and contraction of an IFA connected thereto as discussed above. The catheter 2160 also includes an ultrasound array 2170 which can be used to scan the tissue in which the catheter 2160 is inserted. In some embodiments according to the present invention, both the OCT scanner and the ultrasound transducer image in two or three dimensions. In further embodiments according to the present invention, the OCT scanner and the ultrasound transducer are angled towards each other in the catheter 2160 to scan the same area of tissue. For a two dimensional system, the OCT scanner can be implemented as described above in relation to the optical scanners. For a three dimension system, a cardano suspension, as discussed in reference to FIG. 7, maybe used to pivot the reflector in two dimensions.

Figure 22:
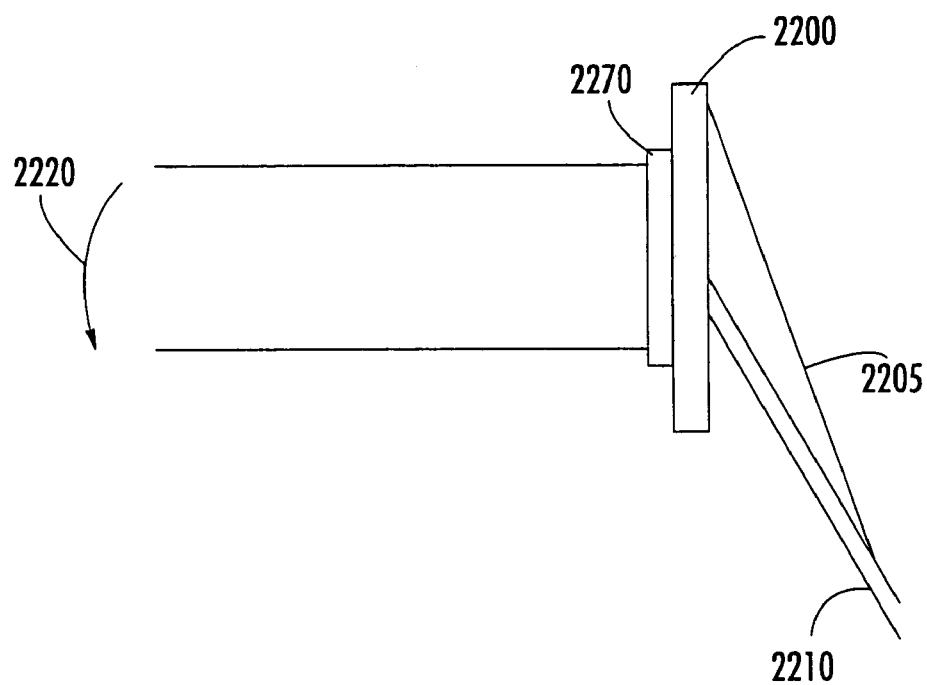
FIG. 22 is a schematic diagram that illustrates scanner devices according to embodiments of the present invention.

FIG. 22 is a schematic diagram that illustrates scanning devices according to embodiments of the present invention. In particular, an electromagnetic radiation device 2200 has an organic light emitting diode (LED) 2270 mounted thereon. The electromagnetic radiation device 2200 is moveably coupled to a member 2210 by a hinge (which is not shown). An IFA 2205 is configured to pivot the electromagnetic radiation device 2200 about the hinge in a plane of movement 2220 by contracting and expanding the IFA 2205. The organic LED 2270 generates electromagnetic radiation which pivots as the electromagnetic radiation device 2200 pivots in the plane of movement 2220.

Figure 23:
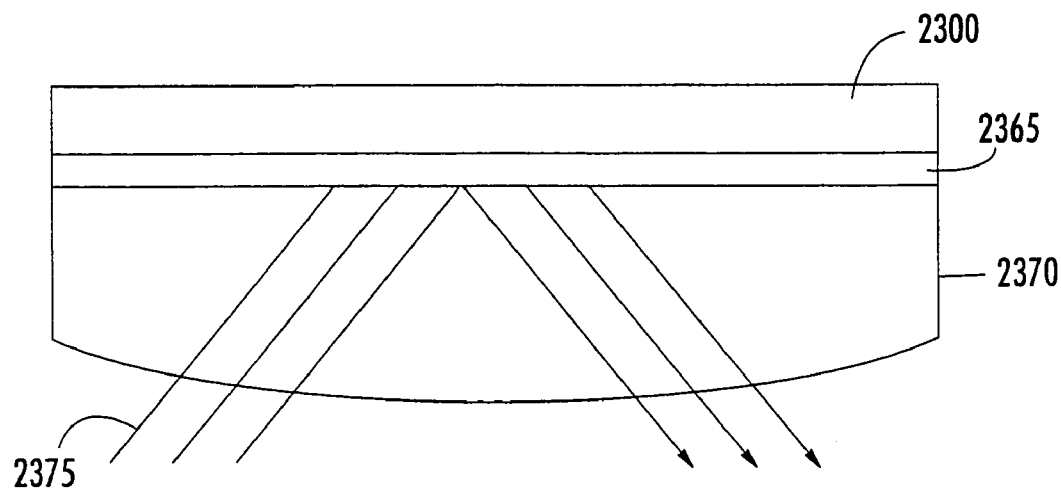
FIGS. 23 to 26 are cross-sectional views that illustrate electromagnetic radiation devices according to embodiments of the present invention.

The reflectors described herein can be fabricated to focus the electromagnetic radiation as well as reflect it. FIG. 23 is a cross-sectional view that illustrates embodiments of focusing reflectors according to the present invention. In particular, a substrate 2300, such as polyimide, has a reflective layer 2365, such as a metal, formed thereon. An optically transparent layer 2370 is on the reflective layer 2365. The optically transparent layer 2370 has a convex surface that is configured to face away from the reflective layer 2365. Electromagnetic radiation 2375 passes through the optically transparent layer 2670 and reflects from the reflective layer 2365. The convex shape of the optically transplant layer 2370 is configured to focus the electromagnetic radiation 2375 reflected therefrom. Moreover, the reflector 2300 can be pivoted as discussed above, to scan the electromagnetic radiation 2375 in a plane of movement to focus the electromagnetic radiation on a target.

Figure 24:
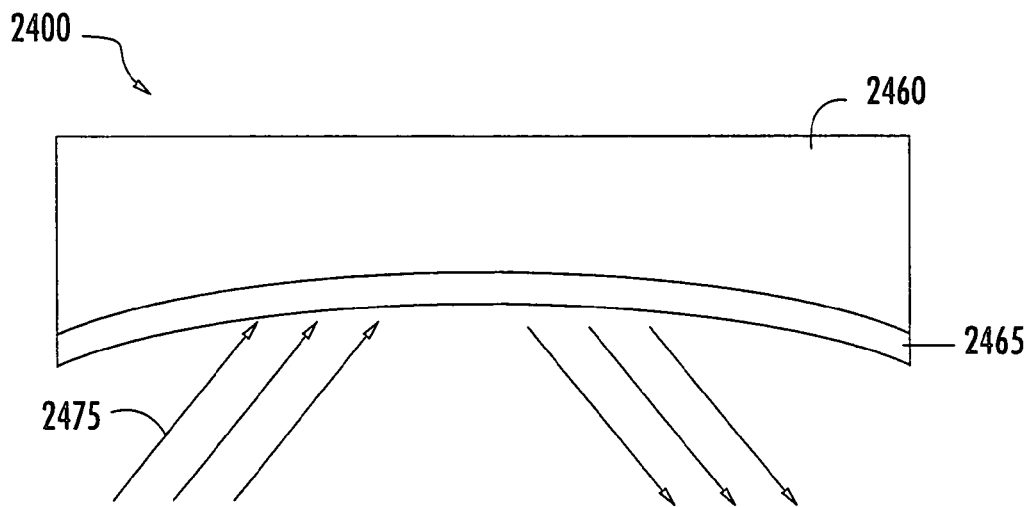

FIG. 24 is a cross-sectional view that illustrates focusing reflectors 2400 according to embodiments of the present invention. In particular, the reflector 2400 includes a substrate 2460, such as a silicon, that is configured to have a concave shape. A reflective layer 2465 is on the concave shaped surface of the substrate 2460. Electromagnetic radiation 2475 is reflected from the reflective layer 2465 and is focused by the concave shape of the reflective layer 2465.

Figure 25A:
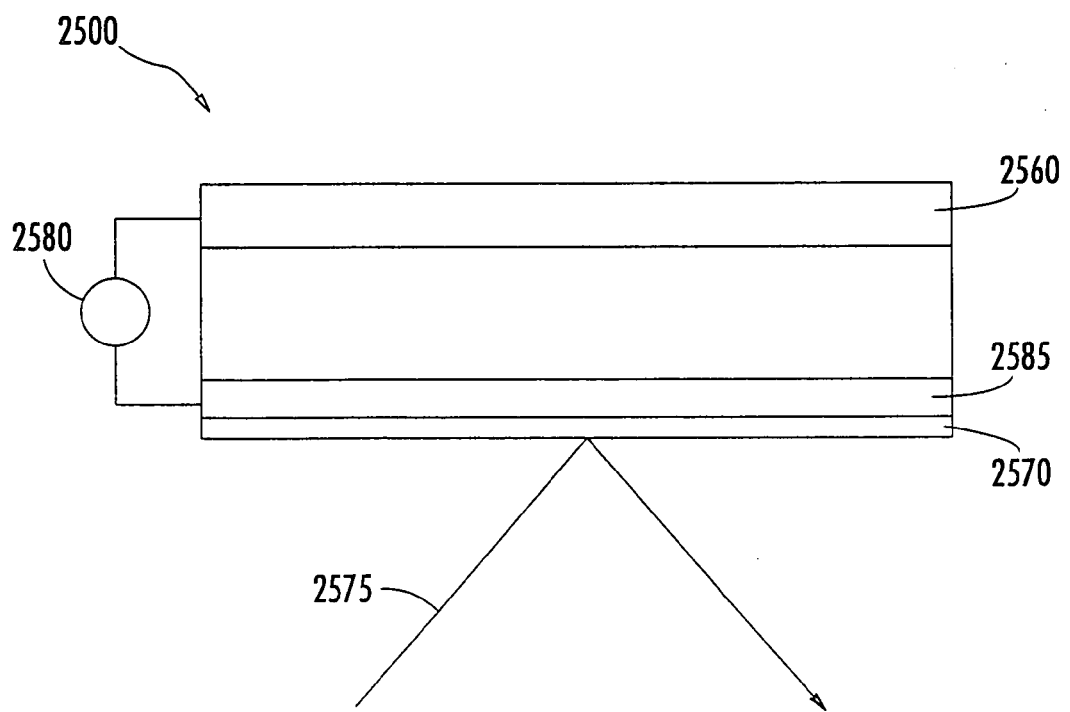
Figure 25B:
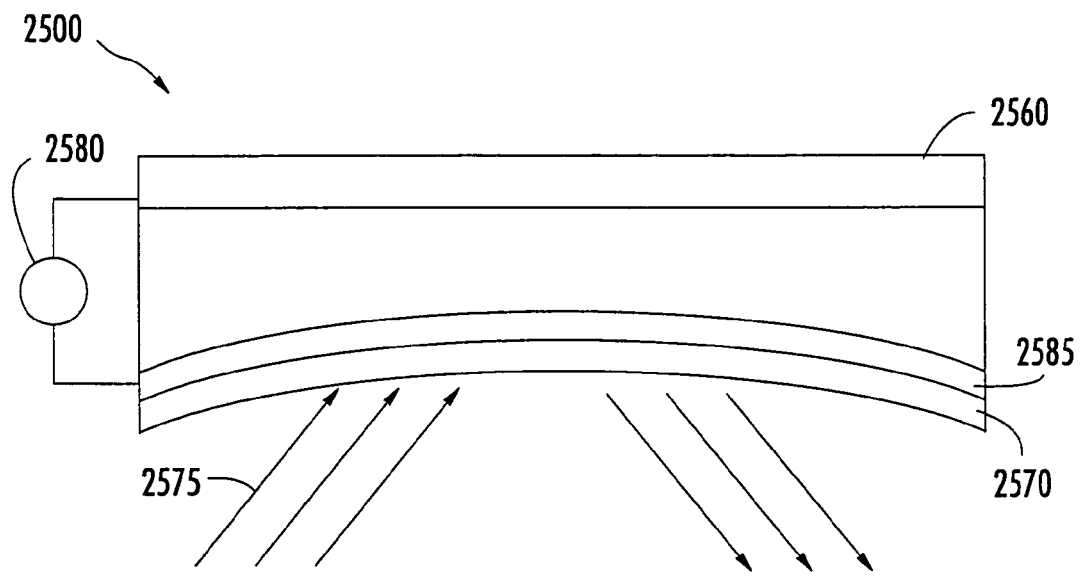

FIGS. 25A and 25B are cross-sectional views that illustrate focusing reflectors 2500 according to embodiments of the present invention including a flexible membrane 2585 that deflects to assume a concave shape. In particular, as shown in FIG. 25A, a reflector 2500 includes a substrate layer 2560 that is a electrically coupled to a voltage source 2580. The flexible membrane 2585 is spaced-apart from the substrate layer 2560 and has a reflective layer 2570 thereon that faces away from the substrate layer 2560. The flexible membrane 2585 is electrically coupled to the voltage supply 2580. In operation, when little or no voltage is provided by the voltage supply 2580, the flexible membrane 2585 assumes a planer shape as shown.

According to FIG. 25B, when the voltage supply 2580 generates an electrostatic force sufficient to deflect the flexible membrane 2585, the flexible membrane 2585 deflects towards the substrate 2560 so that the flexible membrane 2585 assumes a concave shape that faces away from the substrate 2560. Electromagnetic radiation 2575 reflects from the reflective surface 2570 which is configured to focus electromagnetic radiation 2575 due to the concave shape of the reflective layer 2570. Accordingly, a reflector 2500 according to the present invention can provide a planer shape reflective layer to reflect electromagnetic radiation as well as a concave shaped reflector to reflect and focus electromagnetic radiation depending on the voltage provided to the reflector 2500.

Figure 26:
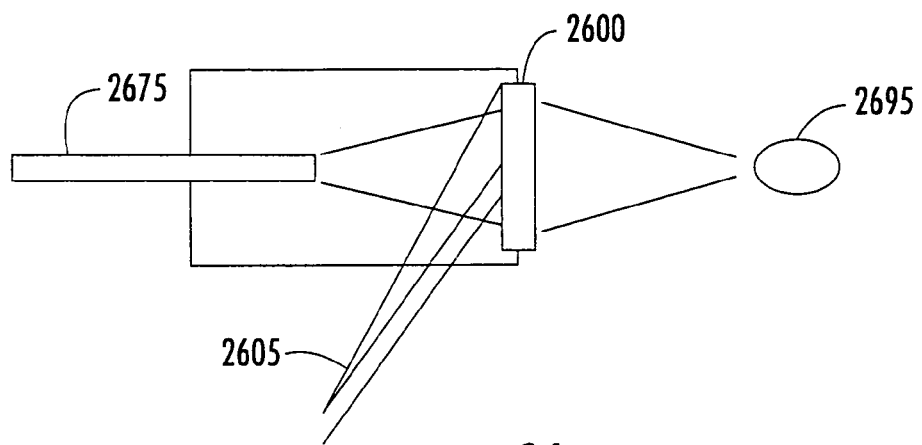

In further embodiments according to the present invention, as shown in FIG. 26, the electromagnetic radiation device can be a lens 2600 through which electromagnetic radiation is passed to focus the electromagnetic radiation on a target 2695. Electromagnetic radiation 2675 is provided to a lens 2600. The electromagnetic radiation 2675 passes through the lens 2600 which is configured to focus the electromagnetic radiation on a target 2695. The lens 2600 can be mounted in an optical scanning system such as those described above, to pivot the lens 2600 using an IFA 2605 so that the electromagnetic radiation focused by the lens 2600 can scan the target. The lens 2600 is coupled to the electromagnetic radiation source 2675 and moves with the lens 2600 as the IFA pivots the lens 2600. In some embodiments according to the present invention, the lens 2600 is a Fresnel lens of hologram that is fabricated in silicon or polymer using, for example, photolithography.

Figure 27:
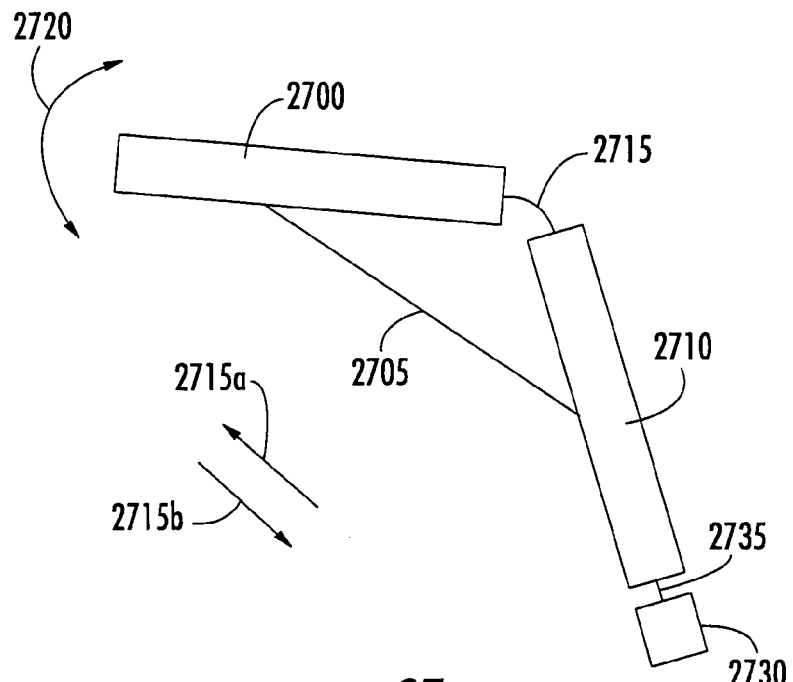
FIGS. 27 to 30 are schematic diagrams that illustrate pivoting members according to embodiments of the present invention.

In further embodiments according to the present invention, the electromagnetic radiation devices described in the embodiments herein can be replaced by a second member that is moveably coupled to the first member and coupled together by an IFA. For example, FIG. 27 is a schematic diagram that illustrates embodiments according to the present invention. In particular, a first member 2710 is moveably coupled to a second member 2700 by a hinge 2715. One end of an IFA 2705 is coupled to a first side of the first member 2710 and a second end of the IFA 2705 is coupled to a first side of the second member 2700 as shown in FIG. 27. The IFA 2705 is configured to expand and contract in directions 2715*a* and 2715*b* to pivot the second member 2700 about the hinge 2715. The hinge 2715 can be a flexion type hinge to allow the second member 2700 to pivot about the hinge 2715 in a plane of movement 2720. Accordingly, the first and second members 2710, 2700 can function as an arm where the hinge 2015 functions as an elbow joint.

Furthermore, a third member 2730 can be moveably coupled to the first member 2710 by a second hinge 2735 that is configured to rotate in a plane of movement that is oriented out of the plane with respect to the plane of movement 2720. The second hinge 2735 provides the function of a wrist joint between the second and third members 2710, 2730. The second hinge can be a torsion type hinge.

The rotation for the third member 2730 can be provided by a second IFA (not shown) that is coupled to the first and third members 2710, 2730. One end of the second IFA is coupled the first member 2710 at a point thereof that is on a first side of the hinge. The other end of the second IFA is coupled to the third member 2730 at a point thereof that is on a second side of the hinge that is opposite the first side. For example, in some embodiments where the second hinge is a torsion hinge that is rectangular, the second IFA is coupled to the first member 2710 at a point thereon that is below the hinge. The other end of the second IFA is coupled to the third member 2730 at a point thereon that is above the hinge.

Figure 28A:
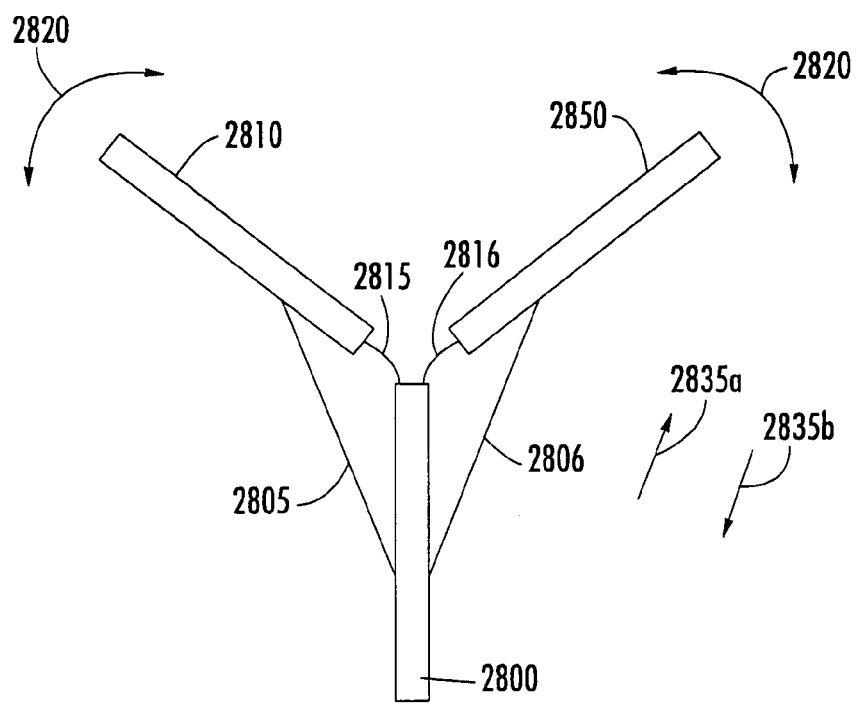

In still further embodiments according to the present invention, as shown in FIG. 28A, a first member 2800 is moveably coupled to a second member 2810 by a first hinge 2815. The first member 2800 is also moveably coupled to a third member 2850 by a second hinge 2816 that is adjacent to the first hinge 2815. One end of a first IFA 2805 is coupled to a first side of the first member 2800 and the other end of the first IFA 2805 is coupled to a first side of the second member 2810. One end of a second IFA 2806 is coupled to a second side of the first member 2800 that is opposite to the point where the first IFA 2805 is coupled. The other end of the second IFA 2806 is coupled to the third member 2850.

The first and second IFAs 2805, 2806 are configured to expand and contract in the directions 2825*a-b* to pivot the second and third members 2810, 2850 about the hinges 2815, 2816 in a plane of movement 2820. The first and second IFAs 2805, 2806 are configured to expand and contract in cooperation with one another so that the second and third members 2810, 2850 can move in a flapping pattern.

Figure 28B:
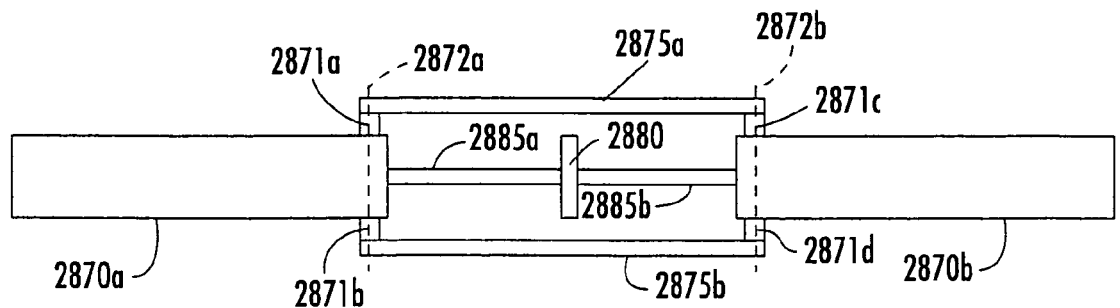

FIG. 28B is a top view that illustrates embodiments of robotic structures according to the present invention. As shown in FIG. 28B, a first wing member 2870*a* is moveably coupled to first and second connecting members 2875*a-b* by first and second hinges 2871*a-b* that define a first axis 2871*a* therethrough about which the first wing member 2870*a* pivots. A second wing member 2870*a* is moveably coupled to the first and second connecting members 2875*a-b* by third and fourth hinges 2871*c-d* that define a second axis 2871*b* therethrough about which the second wing member 2870*b* pivots. The binges can be torsion type hinges. Other types of hinges can be used.

An anchor 2880 is coupled to the first and second wing members 2870*a-b* by first and second IFAs 2885*a-b* respectively. The first and second IFAs 2885*a-b* are coupled to the first and second wing members 2870*a-b* at points thereon that are located between the anchor 2880 and the first and seconds axes 287*a-b*. According to FIG. 28B, the robotic structures illustrated therein can be fabricated, for example, on silicon using photolithography and configured for operation as shown in FIG. 28C.

Figure 28C:
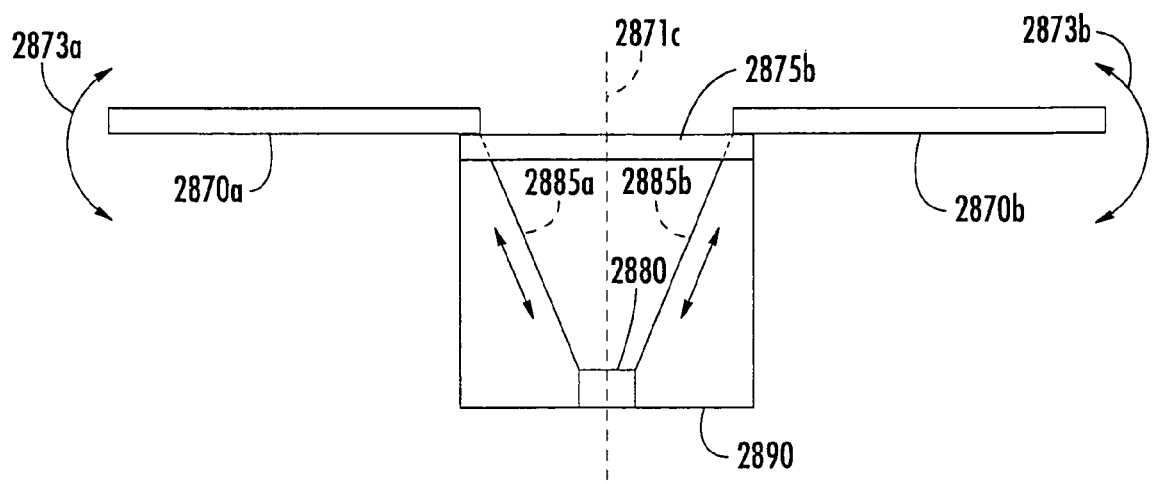

FIG. 28C is a schematic diagram that illustrates embodiments of robotic structures according to the present invention According to FIG. 28C, the anchor 2880 is positioned beneath the first and second wing members 2870*a-b* and the first and second connecting members 2875*a-b*. The anchor 2880 is coupled to first and second connecting members 2875*a-b* by a frame 2890. The first and second IFAs 2885*a-b* are configured to expand and contract to pivot the first and second wing members 2870*a-b* in the planes of movement 2873*a-b* respectively. Accordingly, the embodiments according to the present invention illustrated by FIGS. 28A-28C can provide robotic structures that may operate similar to a bird's or insect's wings.

Figure 28D:
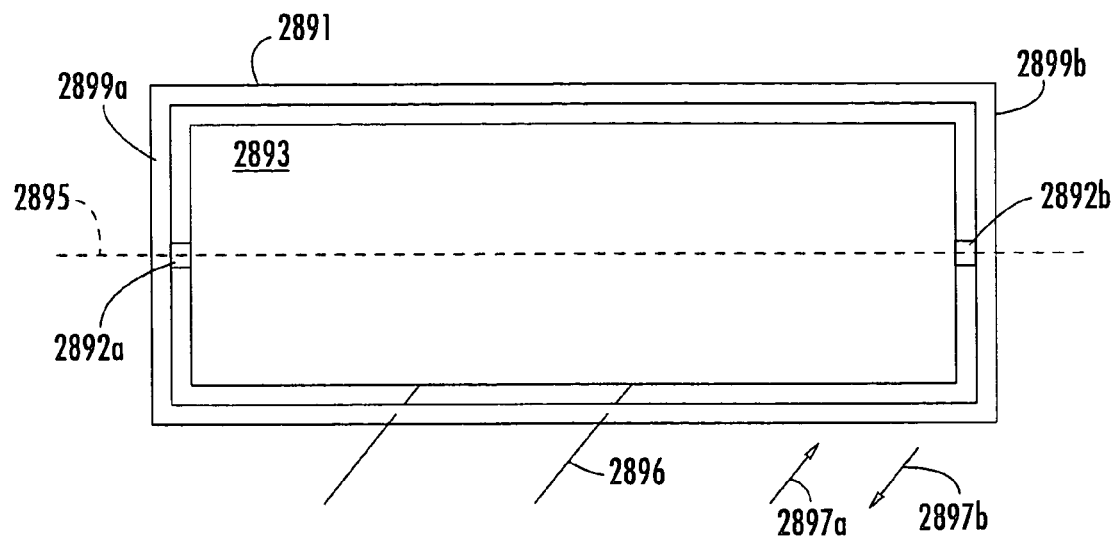

FIG. 28D is a schematic diagram that illustrates embodiments of robotic wing members according to the present invention. As shown in FIG. 28D, a wing member 2893 is located in an interior region of a frame 2891 having first and second opposing portions 2899*a-b*. The wing member 2893 is moveably coupled to the first and second opposing portions 2899*a-b* of the frame 2891 by first and second hinges 2892*a-b* respectively that define an axis 2895 that passes therethrough. An IFA 2896 is coupled to the wing member 2893 at a portion thereof that is spaced apart from the axis 2895. The IFA is configured to expand and contract in the directions 2897*a-b* respectively to pivot the wing member 2893 on the first and second hinges about the axis 2895.

It will be understood that the embodiments of robotic structures according to the present invention illustrated in FIG. 28D can be used as the wing members discussed above in reference to FIGS. 28B and 28C. Accordingly, embodiments of robotic structures according to the present invention can be configured to pivot in one plane of movement (for example, an up and down flapping motion) and simultaneously pivot in a second plane of movement such as the pivoting of the wing member 2893 about the axis 2895.

Figure 29A:
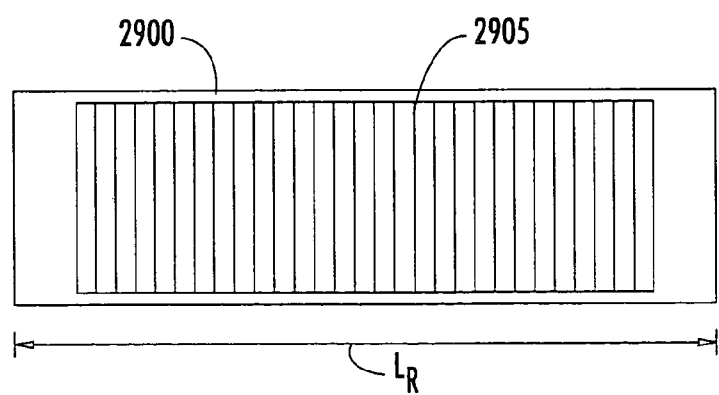
Figure 29B:
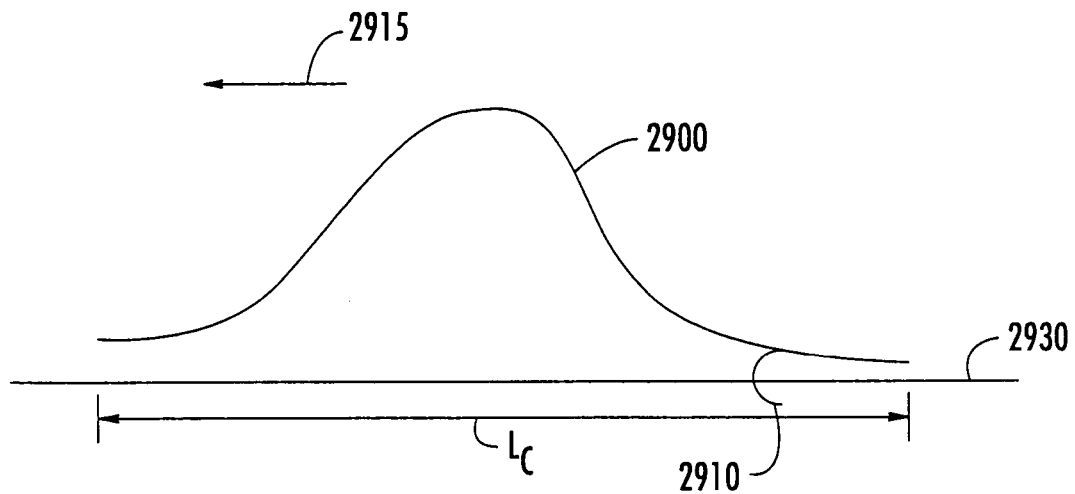

FIG. 29A is a top view that illustrates embodiments according to the present invention. In particular, FIG. 29A shows a flexible substrate 2900 having a first length. An IFA 2905 is on the flexible substrate 2900 and has a first length $L_R$ when the IFA 2905 is in a relaxed state. When the IFA 2905 contracts to a contracted state, the IFA causes the flexible substrate 2900 to arch as shown in FIG. 29B wherein the length of the flexible substrate 2900 is reduced to $L_C$. A latch 2910, or other such translation prevention member, is on a side of the flexible substrate 2900 and is configured to engage a surface 2930 when the IFA 2905 transitions from the contracted state to the relaxed state. For example, when the IFA 2905 is in the contracted state, the flexible substrate 2900 and the IFA 2905 arch as shown in FIG. 29B. When the IFA 2905 transitions to the relaxed state, the flexible substrate 2900 and the IFA 2905 straighten causing the latch 2910 to engage the surface 2930 thereby causing the structure to advance along the surface 2930 in a direction 2915 when the IFA 2905 transitions from the contracted state to the relaxed state. In some embodiments according to the present invention, the latch 2910 can be a ratchet, a fish scale type arrangement commonly used on the underside of skis, mohair, or the like. Accordingly, the embodiments of robotic structures according to the present invention illustrated by FIGS. 29A and 29B can approximate a crawling movement.

Figure 30:
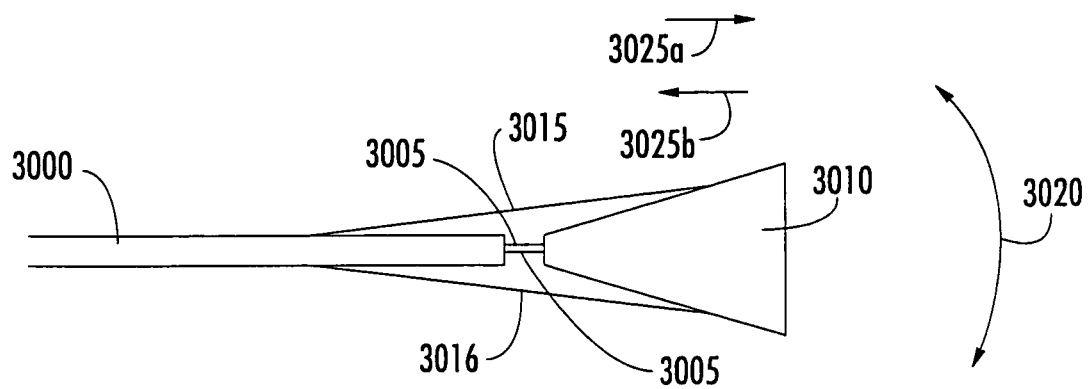

FIG. 30 is a plan view that illustrates embodiments according to the present invention. In particular, a first member 3000 is moveably coupled to a second member 3010 by a hinge 3005. A first IFA 3015 is coupled to a first side of the first member 3000 and a first side of a second member 3010. The IFA 3015 is configured to contract and expand in the directions 3025a-b thereby causing the second member 3010 to pivot about the hinge 3005 in a plane of movement 3020. A second IFA 3016 Iis coupled to the first and second members 3000, 3010 at points thereon which are opposite to the points where the first IFA 3015 is coupled to the first and second members 3000, 3010. The first and second IFAs 3015, 3016 are configured to alternately expand and contract thereby causing the second member 3010 to pivot in a first direction in the plane of movement 3020 and then in a second direction opposite to the first direction in the plane of movement 3020. Accordingly, the embodiments of robotic structures according to the present invention illustrated by FIG. 30 can approximate a fishtail or swimming movement.

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed:

1. A scanner apparatus comprising:
   a member having spaced apart proximal and distal portions;
   an electromagnetic radiation device, configured to direct electromagnetic radiation, moveably coupled to the distal portion of the member and configured to move in a first plane of movement to a first position to direct the electromagnetic radiation along a first path and configured to move in the plane of movement to a second position to direct the electromagnetic radiation along a second path; and
   a MicroElectroMechanical Systems (MEMS) actuator coupled to the electromagnetic radiation device, wherein the MEMS actuator is configured to move in a first direction to move the electromagnetic radiation device to the first position and configured to move in a second direction to move the electromagnetic radiation device to the second position, wherein the MEMS actuator comprises an integrated force array actuator, wherein the electromagnetic radiation device comprises a reflector, wherein the scanner apparatus further comprises:
   an electromagnetic radiation source that projects electromagnetic radiation on the reflector; and
   an ultrasound source on the reflector that is configured to generate ultrasonic radiation.

2. A scanner apparatus according to claim 1 further comprising:
   a hinge that moveably couples the electromagnetic radiation device to the distal portion of the member, wherein the electromagnetic radiation device pivots in the plane of movement about the hinge when the electromagnetic radiation device is moved by MEMS actuator.

3. A scanner apparatus according to claim 2 wherein the hinge comprises one of a torsion hinge and a flexion hinge.

4. A scanner apparatus according to claim 2 wherein the hinge comprises polyimide.

5. A scanner apparatus according to claim 1:
   wherein the MEMS actuator has proximal and distal portions; and
   wherein the distal portion of the MEMS actuator is coupled to the member.

6. A scanner apparatus according to claim 5 wherein the distal portion of the MEMS actuator is coupled to the proximal portion of the member.

7. A scanner apparatus according to claim 1 further comprising:
   a frame coupled to the distal portion of the member, the frame having first and second opposing portions;
   a first hinge that moveably couples the electromagnetic radiation device to the first opposing portion of the frame; and
   a second hinge that moveably couples the electromagnetic radiation device to the second opposing portion of the frame, wherein the first and second hinges define an axis therethrough about which the electromagnetic radiation device pivots in the plane of movement when the electromagnetic radiation device is moved by MEMS actuator.

8. A scanner apparatus according to claim 1 wherein the MEMS actuator comprises a first MEMS actuator, the scanner apparatus further comprising:
   a first frame coupled to the distal portion of the member, the first frame having two opposing portions that define an interior region the first frame;
   first and second hinges on the first and second opposing portions of the first frame respectively, wherein the first and second hinges define a first axis therethrough;
   a second frame in the interior region of the first frame and coupled to the first MEMS actuator, the second frame defining an interior region of the second frame within which the electromagnetic radiation device is located, wherein the second frame has first and second opposing portions, wherein the second frame is movably coupled to the first frame by the first and second hinges to pivot about the first axis when moved by the first MEMS actuator;
   third and fourth hinges that moveably couple the first and second opposing portions of the second frame to the electromagnetic radiation device, wherein the third and fourth hinges define a second axis therethrough that is substantially orthogonal to the first axis; and
   a second MEMS actuator coupled to the electromagnetic radiation device, wherein the second MEMS actuator is configured to pivot the electromagnetic radiation device about the second axis when moved.

9. A scanner apparatus according to claim 1 wherein the electromagnetic radiation device comprises a reflector, wherein the scanner apparatus further comprises:
   an electromagnetic radiation source that projects electromagnetic radiation on the reflector, wherein the electromagnetic radiation source is selected from the list consisting of a laser light source, a confocal microscope system, an ultraviolet light source, an infrared light source, an image data source, and an Alexandrite laser.

10. A scanner apparatus according to claim 1 wherein the reflector comprises gold.

11. A scanner apparatus comprising:
    a member having spaced apart proximal and distal portions;
    an electromagnetic radiation device, configured to direct electromagnetic radiation, moveably coupled to the distal portion of the member and configured to move in a first plane of movement to a first position to direct the electromagnetic radiation alone a first path and configured to move in the plane of movement to a second position to direct the electromagnetic radiation along a second path; and
    a MicroElectroMechanical Systems (MEMS) actuator coupled to the electromagnetic radiation device, wherein the MEMS actuator is configured to move in a first direction to move the electromagnetic radiation device to the first position and configured to move in a second direction to move the electromagnetic radiation device to the second position, wherein the electromagnetic radiation device comprises a focusing reflector that reflects electromagnetic radiation projected thereon to direct reflected electromagnetic radiation along a path, wherein the electromagnetic radiation is focused at a distance from the focusing reflector along the path.

12. A scanner apparatus according to claim 11, the focusing reflector further comprising:
   a substrate layer;
   a reflective layer on the substrate layer;
   an optically transparent layer, on the reflective layer, having a convex surface configured to face away from the reflective layer, wherein the electromagnetic radiation passes through the optically transparent layer to the reflective layer and reflects from the reflective layer through the optically transparent layer along the path.

13. A scanner apparatus according to claim 11, the focusing reflector further comprising:
   a substrate layer having a concave surface; and
   a reflective layer on the concave surface, wherein the electromagnetic radiation reflects from the reflective layer along the path.

14. A scanner apparatus according to claim 11, the focusing reflector further comprising:
   a voltage supply that generates a voltage level;
   a substrate layer electrically coupled to the voltage supply;
   a flexible membrane layer spaced apart from the substrate layer and electrically coupled to the voltage supply, wherein the flexible membrane is configured to deflect towards the substrate layer to assume a concave shape in response to the voltage level;
   a reflective layer on the flexible membrane layer that is configured to reflect the electromagnetic radiation along the path.

15. A scanner apparatus according to claim 1 wherein the electromagnetic radiation device comprises a lens, wherein the scanner apparatus further comprises:
   an electromagnetic radiation source that projects electromagnetic radiation through the lens along the path.

16. A scanner apparatus according to claim 1 wherein the electromagnetic radiation device comprises one of a LED, a semiconductor laser, and an incandescent light that is configured to direct the electromagnetic radiation along the path.

17. A scanner apparatus according to claim 11 further comprising:
   a hinge that moveably couples the electromagnetic radiation device to the distal portion of the member, wherein the electromagnetic radiation device pivots in the plane of movement about the hinge when the electromagnetic radiation device is moved by the MEMS actuator.

18. A scanner apparatus according to claim 17 wherein the hinge comprises one of a torsion hinge and a flexion hinge.

19. A scanner apparatus according to claim 17 wherein the hinge comprises polyimide.

20. A scanner apparatus according to claim 11:
   wherein the MEMS actuator has proximal and distal portions; and
   wherein the distal portion of the MEMS actuator is coupled to the member.

21. A scanner apparatus according to claim 20 wherein the distal portion of the MEMS actuator is coupled to the proximal portion of the member.

22. A scanner apparatus according to claim 11 further comprising:
   a frame coupled to the distal portion of the member, the frame having first and second opposing portions;
   a first hinge that moveably couples the electromagnetic radiation device to the first opposing portion of the frame; and
   a second hinge that moveably couples the electromagnetic radiation device to the second opposing portion of the frame, wherein the first and second hinges define an axis therethrough about which the electromagnetic radiation device pivots in the plane of movement when the electromagnetic radiation device is moved by the MEMS actuator.

23. A scanner apparatus according to claim 11 wherein the MEMS actuator comprises a first MEMS actuator, the scanner apparatus further comprising:
   a first frame coupled to the distal portion of the member, the first frame having two opposing portions that define an interior region of the first frame;
   first and second hinges on the first and second opposing portions of the first frame respective, wherein the first and second hinges define a first axis therethrough;
   a second frame in the interior region of the first frame and coupled to the first MEMS actuator, the second frame defining an interior region of the second frame within which the electromagnetic radiation device is located, wherein the second frame has first and second opposing portions, wherein the second frame is movably coupled to the first frame by the first and second hinges to pivot about the first axis when moved by the first MEMS actuator;
   third and fourth hinges that moveably couple the first and second opposing portions of the second frame to the electromagnetic radiation device, wherein the third and fourth hinges define a second axis therethrough that is substantially orthogonal to the first axis; and
   a second MEMS actuator coupled to the electromagnetic radiation device, wherein the second MEMS actuator is configured to pivot the electromagnetic radiation device about the second axis when moved.

24. A scanner apparatus according to claim 11 wherein the scanner apparatus further comprises:
   an electromagnetic radiation source that projects electromagnetic radiation on the reflector, wherein the electromagnetic radiation source is selected from the list consisting of a laser light source, a confocal microscope system, an ultraviolet light source, an infrared light source, an image data source, and an Alexandrite laser.

25. A scanner apparatus according to claim 11 wherein the scanner apparatus further comprises:
   an electromagnetic radiation source that projects electromagnetic radiation on the reflector; and
   an ultrasound source on the reflector that is configured to generate ultrasonic radiation.

26. A scanner apparatus according to claim 25 wherein the reflector comprises gold.

* * * * *

UNITED STATES PATENT AND TRADEMARK OFFICE
CERTIFICATE OF CORRECTION

PATENT NO. : 7,420,724 B2  
APPLICATION NO. : 10/380791  
DATED : September 2, 2008  
INVENTOR(S) : Smith et al.

Page 1 of 1

It is certified that error appears in the above-identified patent and that said Letters Patent is hereby corrected as shown below:

Column 7, Line 62: Please note new paragraph:
"barcode of FIG. 11A FIG. 12 is a schematic diagram that"
Should read:
-- barcode of FIG. 11A.
    FIG. 12 is a schematic diagram that --

Column 14, Claim 11, Line 60: Please correct "radiation alone a first path"
To read -- radiation along a first path --

Column 15, Claim 16, Line 43: Please correct "of a LED" to read -- of an LED --

Signed and Sealed this

Eleventh Day of November, 2008

JON W. DUDAS  
*Director of the United States Patent and Trademark Office*